US009656095B2

(12) United States Patent
Watson et al.

(10) Patent No.: US 9,656,095 B2
(45) Date of Patent: May 23, 2017

(54) HARMONIC COLD PLASMA DEVICES AND ASSOCIATED METHODS

(71) Applicant: Plasmology4, Inc., Scottsdale, AZ (US)

(72) Inventors: Gregory A. Watson, Lake Mary, FL (US); Robert M. Hummel, Cave Creek, AZ (US); Marc C. Jacofsky, Phoenix, AZ (US); David J. Jacofsky, Peoria, AZ (US)

(73) Assignee: Plasmology4, Inc., Scottsdale, AZ (US)

( * ) Notice: Subject to any disclaimer, the term of this patent is extended or adjusted under 35 U.S.C. 154(b) by 0 days.

(21) Appl. No.: 14/949,469

(22) Filed: Nov. 23, 2015

(65) Prior Publication Data
US 2016/0106993 A1    Apr. 21, 2016

Related U.S. Application Data

(63) Continuation-in-part of application No. 13/620,236, filed on Sep. 14, 2012, now Pat. No. 9,192,776.
(Continued)

(51) Int. Cl.
*B23K 10/00* (2006.01)
*A61N 1/44* (2006.01)
(Continued)

(52) U.S. Cl.
CPC .............. *A61N 1/44* (2013.01); *A61L 2/0094* (2013.01); *A61L 2/14* (2013.01); *A61M 15/02* (2013.01);
(Continued)

(58) Field of Classification Search
CPC ....... A61N 1/44; A61M 35/003; A61M 25/00; A61M 2202/048; A61M 2202/0208;
(Continued)

(56) References Cited

U.S. PATENT DOCUMENTS

| 2,927,322 A | 3/1960 | Simon et al. |
| 3,432,722 A | 3/1969 | Naydan et al. |

(Continued)

FOREIGN PATENT DOCUMENTS

| WO | WO 00/70117 | 11/2000 |
| WO | WO 2005/084569 A1 | 9/2005 |

(Continued)

OTHER PUBLICATIONS

Dumé, Belle, "Cold Plasmas Destroy Bacteria," article, [online], [retrieved on Jan. 5, 2007], Retrieved from the PhysicsWeb website using Internet <URL:http://physicsweb.org/articles/news7/4/19>.
(Continued)

*Primary Examiner* — Mark Paschall
(74) *Attorney, Agent, or Firm* — Sterne, Kessler, Goldstein & Fox P.L.L.C.

(57) ABSTRACT

A nozzle for attachment to a cold plasma device configured to maintain delivery of a stable cold plasma. The nozzle can have many different shaped apertures to support different applications requiring different shaped cold plasma plumes. Use of a disc of foam material within a nozzle can expand the size of aperture of a nozzle while maintaining delivery of a stable cold plasma. The nozzle can be an elongated cannula tube for internal delivery of a cold plasma treatment. The cannula tube can provide an aperture at its distal end or one or more apertures along its length. A shroud can partially enclose the distal aperture of the nozzle. A sterile sleeve can be used in conjunction with a nozzle to provide a sterile means of attachment and operation of the nozzle with a cold plasma device. In addition, various shaped apertures may be deployed to provide selective targeting of the cold plasma to a treatment area, while shielding other biological structures from cold plasma exposure. Such apertures also provide an
(Continued)

opportunity for manual manipulation of tissues in the treatment area prior to or during cold plasma treatment.

20 Claims, 19 Drawing Sheets

Related U.S. Application Data

(60) Provisional application No. 61/535,250, filed on Sep. 15, 2011.

(51) Int. Cl.
*A61M 35/00* (2006.01)
*A61M 25/00* (2006.01)
*A61M 15/02* (2006.01)
*A61M 16/12* (2006.01)
*A61L 2/00* (2006.01)
*A61L 2/14* (2006.01)
*H05H 1/46* (2006.01)
*H01J 37/32* (2006.01)
*A61N 1/40* (2006.01)

(52) U.S. Cl.
CPC ............ *A61M 16/12* (2013.01); *A61M 25/00* (2013.01); *A61M 35/003* (2013.01); *H01J 37/32825* (2013.01); *H05H 1/46* (2013.01); *A61M 2202/025* (2013.01); *A61M 2202/0208* (2013.01); *A61M 2202/048* (2013.01); *A61N 1/40* (2013.01); *H05H 2001/4682* (2013.01); *H05H 2240/20* (2013.01); *H05H 2245/122* (2013.01); *H05H 2277/10* (2013.01)

(58) Field of Classification Search
CPC .... H05H 1/46; H05H 1/34; H05H 2001/4682; H05H 2277/10; H05H 2240/20; H05H 37/32825
USPC ....... 219/212.5, 121.43, 121.48; 315/111.51; 607/96, 98, 99; 606/41
See application file for complete search history.

(56) References Cited

U.S. PATENT DOCUMENTS

| | | | |
|---|---|---|---|
| 3,487,414 A | 12/1969 | Booker | |
| 3,735,591 A | 5/1973 | Burkhart | |
| 4,088,926 A | 5/1978 | Fletcher et al. | |
| 4,365,622 A | 12/1982 | Harrison | |
| 4,380,320 A | 4/1983 | Hollstein et al. | |
| 4,422,013 A | 12/1983 | Turchi et al. | |
| 4,781,175 A | 11/1988 | McGreevy et al. | |
| 4,866,240 A | 9/1989 | Webber | |
| 5,079,482 A | 1/1992 | Villecco et al. | |
| 5,216,330 A | 6/1993 | Ahonen | |
| 5,225,740 A | 7/1993 | Ohkawa | |
| 5,304,888 A | 4/1994 | Gesley et al. | |
| 5,357,076 A | 10/1994 | Blankenship | |
| 5,381,789 A | 1/1995 | Marquardt | |
| 5,698,164 A | 12/1997 | Kishioka et al. | |
| 5,876,663 A | 3/1999 | Laroussi | |
| 5,883,470 A | 3/1999 | Hatakeyama et al. | |
| 5,909,086 A | 6/1999 | Kim et al. | |
| 5,961,772 A | 10/1999 | Selwyn | |
| 5,977,715 A | 11/1999 | Li et al. | |
| 6,096,564 A | 8/2000 | Denes et al. | |
| 6,099,523 A | 8/2000 | Kim et al. | |
| 6,113,851 A | 9/2000 | Soloshenko et al. | |
| 6,204,605 B1 | 3/2001 | Laroussi et al. | |
| 6,213,999 B1 | 4/2001 | Platt, Jr. et al. | |
| 6,225,593 B1 | 5/2001 | Howieson et al. | |
| 6,228,330 B1 | 5/2001 | Herrmann et al. | |
| 6,262,523 B1 | 7/2001 | Selwyn et al. | |
| 6,441,554 B1 | 8/2002 | Nam et al. | |
| 6,455,014 B1 | 9/2002 | Hammerstrom et al. | |
| 6,611,106 B2 | 8/2003 | Monkhorst et al. | |
| 6,667,007 B1 | 12/2003 | Schmidt | |
| 6,956,329 B2 | 10/2005 | Brooks et al. | |
| 6,958,063 B1 | 10/2005 | Soll et al. | |
| 7,006,874 B2 | 2/2006 | Knowlton et al. | |
| 7,011,790 B2 | 3/2006 | Ruan et al. | |
| 7,033,353 B2 | 4/2006 | Stoddard et al. | |
| 7,037,468 B2 | 5/2006 | Hammerstrom et al. | |
| 7,081,711 B2 | 7/2006 | Glidden et al. | |
| 7,094,314 B2 | 8/2006 | Kurunczi | |
| 7,192,553 B2 | 3/2007 | Crowe et al. | |
| 7,215,697 B2 | 5/2007 | Hill | |
| 7,271,363 B2 | 9/2007 | Lee et al. | |
| 7,300,436 B2 | 11/2007 | Penny et al. | |
| 7,335,199 B2 | 2/2008 | Goble et al. | |
| 7,608,839 B2 | 10/2009 | Coulombe et al. | |
| 7,633,231 B2 * | 12/2009 | Watson ............... | H05H 1/46 219/121.36 |
| 7,683,342 B2 | 3/2010 | Morfill et al. | |
| 7,691,101 B2 | 4/2010 | Davison et al. | |
| 7,719,200 B2 | 5/2010 | Laroussi | |
| 7,777,151 B2 | 8/2010 | Kuo | |
| 7,785,322 B2 | 8/2010 | Penny et al. | |
| 7,799,290 B2 | 9/2010 | Hammerstrom et al. | |
| 8,267,884 B1 | 9/2012 | Hicks | |
| 8,294,369 B1 | 10/2012 | Laroussi | |
| 8,460,283 B1 | 6/2013 | Laroussi et al. | |
| 9,211,603 B2 * | 12/2015 | Severance, Jr. ........ | B23K 10/00 |
| 2002/0129902 A1 | 9/2002 | Babayan et al. | |
| 2003/0222586 A1 | 12/2003 | Brooks et al. | |
| 2005/0088101 A1 | 4/2005 | Glidden et al. | |
| 2005/0179395 A1 | 8/2005 | Pai | |
| 2006/0052772 A1 | 3/2006 | Sartor et al. | |
| 2006/0122560 A1 | 6/2006 | Burgmeier et al. | |
| 2006/0131282 A1 | 6/2006 | Miller et al. | |
| 2006/0189976 A1 | 8/2006 | Karni et al. | |
| 2008/0110532 A1 | 5/2008 | Lotz | |
| 2008/0159925 A1 | 7/2008 | Shimizu et al. | |
| 2009/0061200 A1 | 3/2009 | Hild et al. | |
| 2009/0188626 A1 | 7/2009 | Lu et al. | |
| 2009/0192505 A1 * | 7/2009 | Askew ............... | A61B 18/0218 606/21 |
| 2009/0251319 A1 | 10/2009 | Ichikawa et al. | |
| 2009/0275941 A1 | 11/2009 | Sartor et al. | |
| 2010/0100091 A1 | 4/2010 | Truckai | |
| 2010/0133979 A1 | 6/2010 | Lu | |
| 2010/0145260 A1 | 6/2010 | Watson | |
| 2010/0292757 A1 | 11/2010 | Ehlbeck et al. | |
| 2011/0022043 A1 | 1/2011 | Wandke et al. | |
| 2012/0100524 A1 * | 4/2012 | Fridman ............... | A61L 2/0011 435/2 |
| 2012/0187841 A1 | 7/2012 | Kindel et al. | |
| 2012/0221003 A1 * | 8/2012 | Auge, II ............... | A61B 18/12 606/45 |
| 2012/0259270 A1 | 10/2012 | Wandke et al. | |
| 2013/0022514 A1 | 1/2013 | Morfill et al. | |
| 2013/0053762 A1 * | 2/2013 | Rontal ................. | A61B 1/0051 604/24 |
| 2013/0068732 A1 | 3/2013 | Watson et al. | |
| 2013/0134878 A1 | 5/2013 | Selwyn | |
| 2013/0199540 A1 | 8/2013 | Buske | |
| 2014/0000810 A1 | 1/2014 | Franklin et al. | |
| 2014/0121658 A1 * | 5/2014 | Cosman, Jr. .......... | A61B 18/18 606/33 |
| 2014/0284312 A1 * | 9/2014 | Chen ................. | H05H 1/34 219/121.5 |
| 2014/0303549 A1 * | 10/2014 | Sheperak ............. | A61N 5/10 604/24 |

FOREIGN PATENT DOCUMENTS

| | | |
|---|---|---|
| WO | WO 2006/116252 | 11/2006 |
| WO | WO 2007/124910 A2 | 11/2007 |
| WO | WO 2008/131407 A1 | 10/2008 |
| WO | WO 2010/107722 A1 | 9/2010 |
| WO | WO 2011/015538 A1 | 2/2011 |

(56) References Cited

FOREIGN PATENT DOCUMENTS

| WO | WO 2011/055368 A2 | 5/2011 |
|---|---|---|
| WO | WO 2011/055369 A2 | 5/2011 |
| WO | WO 2011/076193 A1 | 6/2011 |
| WO | WO 2012/106735 A2 | 8/2012 |
| WO | WO 2012/153332 A2 | 11/2012 |
| WO | WO 2013/101673 A1 | 7/2013 |

OTHER PUBLICATIONS

Gould, Phillip and Eyler, Edward, "Ultracold Plasmas Come of Age," article [online], [retrieved on Jan. 5, 2007], Retrieved from the PhysicsWeb website using Internet <URL:http://physicsweb.org/articles/world/14/3/3>.

Schultz, James, "Cold Plasma Ignites Hot Applications," article, [online], [retrieved on Jan. 5, 2007], Retrieved from the Old Dominion University website using Internet <URL:http://www.odu.edu/ao/instadv/quest/coldplasma.html>.

Lamba, Bikram, "Advent of Cold Plasma," article, [online], [retrieved on Jan. 5, 2007], Retrieved from the PhysOrg.com website using Internet <URL:http/www.physorg.com/printnews.php?newsid=6688>.

Book of Abstracts, 3rd International Conference on Plasma Medicine (ICPM-3), Sep. 19-24, 2010, International Society for Plasma Medicine.

International Search Report issued Aug. 6, 2008 for Appl. No. PCT/US2008/061240, 1 page.

Written Opinion of International Searching Authority issued Aug. 6, 2008 for Appl. No. PCT/US2008/061240, 6 pages.

Extended European Search Report issued Feb. 8, 2012 for European Patent Appl. No. EP08746627.2, 7 pages.

Pointu et al., "Nitrogen Atmospheric Pressure Post Discharges for Surface Biological Decontamination inside Small Diameter Tubes," *Plasma Process. Polym.* 5:559-568, Wiley-VCH Verlag GmbH & Co. KGaA, Weinheim (2008).

Chakravarthy et al., "Cold Spark Discharge Plasma Treatment of Inflammatory Bowel Disease in an Animal Model of Ulcerative Colitis," *Plasma Medicine* (1)1:3-19, Begell House, Inc. (2011).

International Search Report mailed Jan. 22, 2013 for Appl. No. PCT/US2012/055595, 5 pages.

Written Opinion of International Searching Authority mailed Jan. 22, 2013 for Appl. No. PCT/US2012/055595, 8 pages.

Fridman et al., "Comparison of Direct and Indirect Effects of Non-Thermal Atmospheric-Pressure Plasma on Bacteria," *Plasma Processl Polym.*, 4, 370-375, 6 pages, Wiley-VCH Verlag GmbH & Co. KGaA, Weinheim (2007).

Alexander Fridman, "Plasma Chemistry," pp. 263-271, Cambridge University Press, 2008, 9 pages.

O'Connell et al., "The role of the relative voltage and phase for frequency coupling in a dual-frequency capacitively coupled plasma," *Applied Physics Letters*, 93 081502, 3 pages, American Institute of Physics (Aug. 25, 2008).

Nie et al., "A two-dimensional cold atmospheric plasma jet array for uniform treatment of large-area surfaces for plasma medicine," *New Journal of Physics*, 11 115015, 14 pages, IOP Publishing Ltd and Deutsche Physikalische Gesellschaft (2009).

Pompl et al., "The effect of low-temperature plasma on bacteria as observed by repeated AFM imaging," *New Journal of Physics*, 11 115023, 11 pages, IOP Publishing Ltd and Deutsche Physikalische Gesellschaft (Nov. 26, 2009).

Walsh et al., "Three distinct modes in a cold atmospheric pressure plasma jet," *J. Phys. D.: Appl. Phys.* 43 075201, 14 pages, IOP Publishing Ltd (Feb. 3, 2010).

Ricci et al., "The effect of stochastic electrical noise on hard-to-heal wounds," *Journal of Wound Care*, 8 pages, 19:3 Mark Allen Publishing Ltd ( Mar. 2010).

U.S. Appl. No. 61/485,747, filed May 13, 2011, inventor Thomas J. Sheperak, 14 pages.

Pompl, et al., "The effect of low-temperature plasma on bacteria as observed by repeated AFM imaging," *New Journal of Physics*, 11 115023, 11 pages, IOP Publishing Ltd and Deutsche Physikalische Gesellschaft (Nov. 26, 2009).

Liu et al., "Sub-60° C. atmospheric helium-water plasma jets: modes, electron heating and downstream reaction chemistry," *J. Phys. D: Appl. Phys.* 44 345203, 13 pages, IOP Publishing Ltd. (Aug. 11, 2011).

Pei et al., "Inactivation of a 25.5 μm *Enterococcus faecalis* biofilm by a room-temperature, battery-operated, handheld air plasma jet," *J. Phys. D. Appl. Phys.*, 45 165205, 5 pages, IOP Publishing Ltd (Apr. 4, 2012).

Walsh et al., "Chaos in atmospheric-pressure plasma jets," *Plasma Sources Sci. Technol.*, 21 034008, 8 pages, IOP Publishing Ltd (May 2, 2012).

Banu, et al., "Cold Plasma as a Novel Food Processing Technology," *International Journal of Emerging trends in Engineering and Development*, Issue 2, vol. 4, ISSN 2249-6149, pp. 803-818, 16 pages (May 2012).

Dobrynin, et al., "Live Pig Skin Tissue and Wound Toxicity of Cold Plasma Treatment," *Plasma Medicine*, 1(1):93-108, 16 pages, Begell House, Inc. (2011).

Fernández, et al., "The inactivation of *Salmonella* by cold atmosphere plasma treatment," *Food Research International*, 45:2, 678-684, 7 pages, Elsevier Ltd. (Mar. 2012).

Tien, et al., "The Bilayer Lipid Membrane (BLM) Under Electrical Fields," *IEEE Transactions on Dielectrics and Electrical Institute*, 10:5, 717-727, 11 pages (Oct. 2003).

Jayaram, et al.., "Optimization of Electroporation Waveforms for Cell Sterilization," *IEEE Transactions on Industry Applications*, 40:6, 1489-1497, 9 pages (2004).

Fridman, et al., "Use of Non-Thermal Atmospheric Pressure Plasma Discharge for Coagulation and Sterilization of Surface Wounds," *IEEE International Conference on Plasma Science*, Abstract, p. 257, 1 page (Jun. 2005).

Fridman, et al., "Use of Non-Thermal Atmospheric Pressure Plasma Discharge for Coagulation and Sterilization of Surface Wounds," 6 pages (Jun. 2005).

Fridman, et al., "Blood Coagulation and Living Tissue Sterilization by Floating-Electrode Dielectric Barrier Discharge in Air," *Plasma Chem Plasma Process*, 26: 425-442, 18 pages, Springer Science Business Media, Inc. (2006).

Gurol, et al., "Low Temperature Plasma for decontamination of *E. coli* in milk," *International Journal of Food Microbiology*, 157: 1-5, 5 pages, Elsevier B.V. (Jun. 2012).

Lado, et al., "Alternative food-preservation technologies: efficacy and mechanisms," *Microbes and Infection*, 4: 433-440 8 pages, Elsevier SAS (2002).

Leduc, et al., "Cell permeabilization using a non-thermal plasma," *New Journal of Physics*, 11: 115021, 12 pages, IOP Publishing Ltd and Deutsche Physikalische Gesellschaft (2009).

Machado, et al., "Moderate electric fields can inactivate *Escherichia coli* at room temperature," *Journal of Food Engineering*, 96: 520-527, 8 pages, Elsevier Ltd. (2009).

Li, et al., "Optimizing the distance for bacterial treatment using surface micro-discharge plasma," *New Journal of Physics*, 14: 023058, 11 pages, IOP Publishing Ltd and Deutsche Physikalische Gesellschaft (Feb. 2012).

Morfill, et al., "Nosocomial infections—a new approach towards preventive medicine using plasmas," *New Journal of Physics*, 11: 115019, 10 pages, IOP Publishing Ltd and Deutsche Physikalische Gesellschaft (2009).

Nian, et al., "Decontamination of *Salmonella* on Sliced Fruits and Vegetables Surfaces using a Direct-Current, Atmospheric-Pressure Cold Plasma," *IEEE International Conference on Plasma Science*, p. 1, 1 page (Jun. 2011).

Toepfl, et al., "High intensity pulsed electric fields applied for food preservation," *Chemical Engineering and Processing*, 46: 537-546, 10 pages, Elsevier B.V. (2007).

The Supplementary European Search Report mailed Feb. 24, 2015 for Appl. No. PCT/US2012/055595, 7 pages.

\* cited by examiner

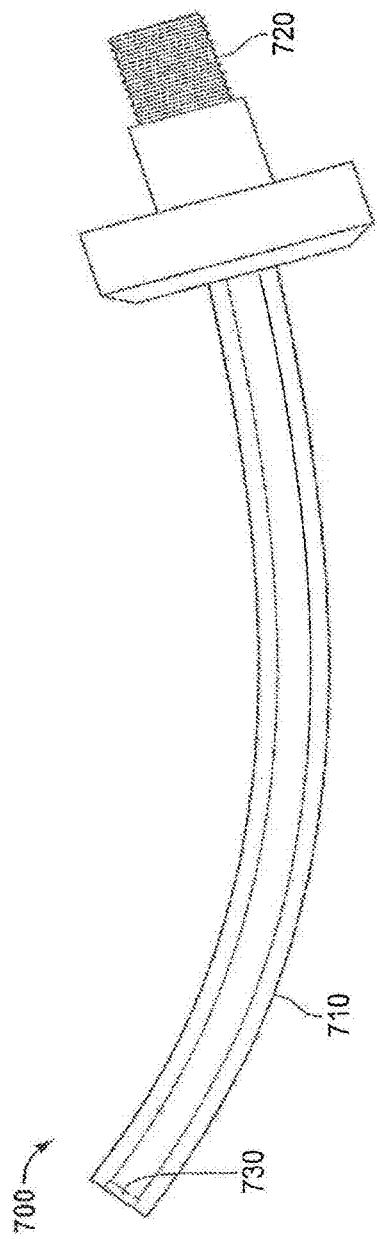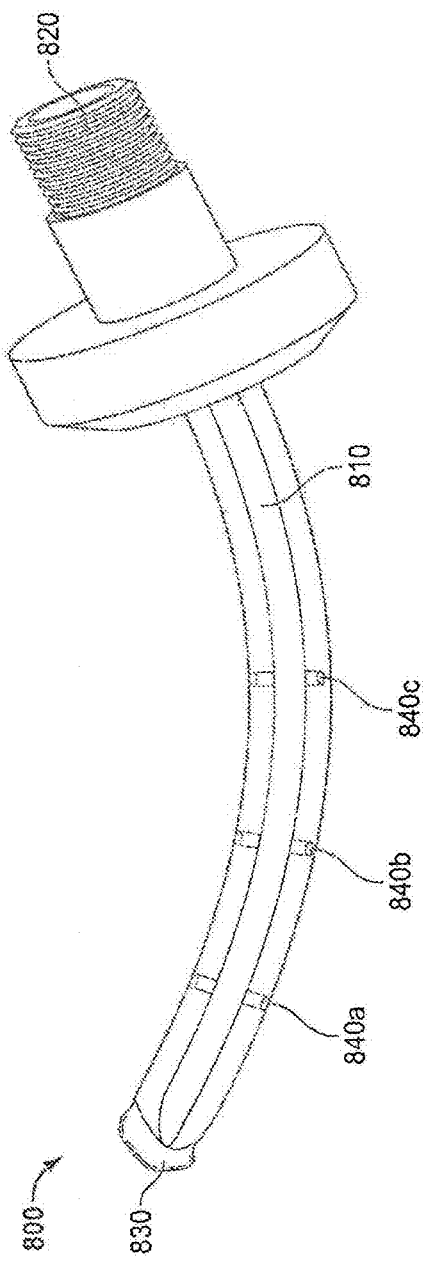
FIG. 7
FIG. 8

2100

US 9,656,095 B2

HARMONIC COLD PLASMA DEVICES AND ASSOCIATED METHODS

CROSS REFERENCE TO RELATED APPLICATIONS

The present application is a continuation-in-part of U.S. Non-Provisional application Ser. No. 13/620,236, filed Sep. 14, 2012, which claims the benefit under 35 U.S.C. §119(e) of U.S. Provisional Patent Application No. 61/535,250, entitled "Harmonic Cold Plasma Devices and Associated Methods", filed on Sep. 15, 2011, all of which are hereby expressly incorporated by reference in their entirety.

This application is related to U.S. patent application Ser. No. 13/149,744, filed May 31, 2011, U.S. patent application Ser. No. 12/638,161, filed Dec. 15, 2009, U.S. patent application Ser. No. 12/038,159, filed Feb. 27, 2008, and U.S. Provisional Application No. 60/913,369, filed Apr. 23, 2007, each of which are herein incorporated by reference in their entireties.

BACKGROUND

Field of the Art

The present invention relates to devices and methods for creating cold plasmas, and, more particularly, to such devices that are hand-held and methods for using same.

Background Art

Atmospheric pressure hot plasmas are known to exist in nature. For example, lightning is an example of a DC arc (hot) plasma. Many dc arc plasma applications have been achieved in various manufacturing processes, for example, for use in forming surface coatings. Atmospheric pressure cold plasma processes are also known in the art. Most of the at or near atmospheric pressure cold plasma processes are known to utilize positive to negative electrodes in different configurations, which release free electrons in a noble gas medium.

Devices that use a positive to negative electrode configuration to form a cold plasma from noble gases (helium, argon, etc.) have frequently exhibited electrode degradation and overheating difficulties through continuous device operation. The process conditions for enabling a dense cold plasma electron population without electrode degradation and/or overheating are difficult to achieve.

Different applications of cold plasma devices require different size cold plasma plumes and different dimensional devices to produce those cold plasma plumes. For example, some medical treatments require a large cold plasma plume to treat a large external wound, while other treatments require a small cold plasma device that can be coupled to an elongated medical device that can traverse a small body passageway to reach a small internal treatment site.

Therefore, it would be beneficial to provide a device for producing a cold plasma that overcomes the difficulties inherent in prior known devices.

BRIEF SUMMARY OF THE INVENTION

Embodiments are described that provide cold plasma for a number of applications including medical applications and the like.

An embodiment of a cold plasma device is described that has a housing having a high voltage electrical inlet port and a gas compartment, with the gas compartment having a gas inlet port and a gas outlet port. The embodiment also has an electrode disposed within the gas compartment, wherein the electrode is coupled to the high voltage electrical inlet port. The embodiment also has a nozzle having a proximal aperture and a distal aperture, the proximal aperture being configured to be coupled to the gas outlet port, and the nozzle being configured to maintain a stable cold plasma plume exiting from the distal aperture.

An embodiment of a cold plasma method is described that includes a step of connecting a nozzle to a cold plasma device, with an attachment mechanism being external to a sterile sleeve, and a remainder of the nozzle enclosed in a sterile sleeve. The embodiment also includes a step of inverting the sterile sleeve over the cold plasma device and attachment mechanism to thereby expose the distal aperture of the nozzle for use.

An embodiment of a cold plasma method is described that includes a step of forming a nozzle configured to couple to a cold plasma device. The embodiment also includes steps of forming a sterile sleeve having an attachment mechanism, attaching a sterile sleeve to the nozzle via the attachment mechanism such that the distal aperture is enclosed in the sterile sleeve, and sterilizing the nozzle and sterile sleeve.

An embodiment of a cold plasma method is described that includes a step of grasping a nozzle through a sterile sleeve such that contact is made with an inner portion of the sterile sleeve. The embodiment also includes steps of attaching the nozzle to a cold plasma device, and inverting the sterile sleeve to enclose the cold plasma device, and a portion of a power cord associated with the cold plasma device.

An embodiment of a cold plasma method is described that includes a step of providing a gas cartridge, with the gas cartridge including a suitable amount of gas, and the gas cartridge having a connector. The embodiment also includes steps of providing a cold plasma hand piece, the cold plasma hand piece having a mating connector to the connector in the gas cartridge, providing a nozzle, the nozzle configured to maintain a stable cold plasma plume exiting from the cold plasma hand piece, connecting the gas cartridge to the cold plasma hand piece using the connector and the mating connector, determining, by the cold plasma hand piece or a pulsed high voltage power supply, a type of nozzle, adjusting one or more operating parameters of the pulsed high voltage power supply based on the type of nozzle, and providing energy to the cold plasma hand piece from the pulsed high voltage power supply.

BRIEF DESCRIPTION OF THE DRAWINGS/FIGURES

FIG. 7 illustrates an exemplary cannula tube for a cold plasma device, in accordance with an embodiment of the present invention.

FIG. 8 illustrates an exemplary cannula tube with one or more apertures along the length of the cannula tube, in accordance with an embodiment of the present invention.

Figure 16B:
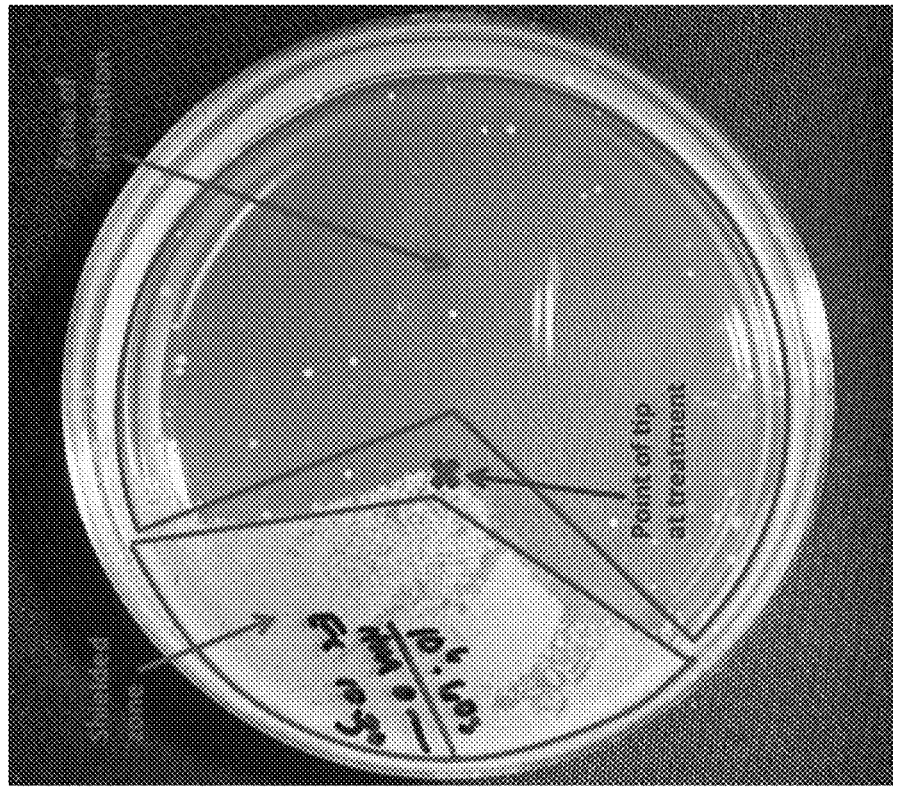
Figure 16A:
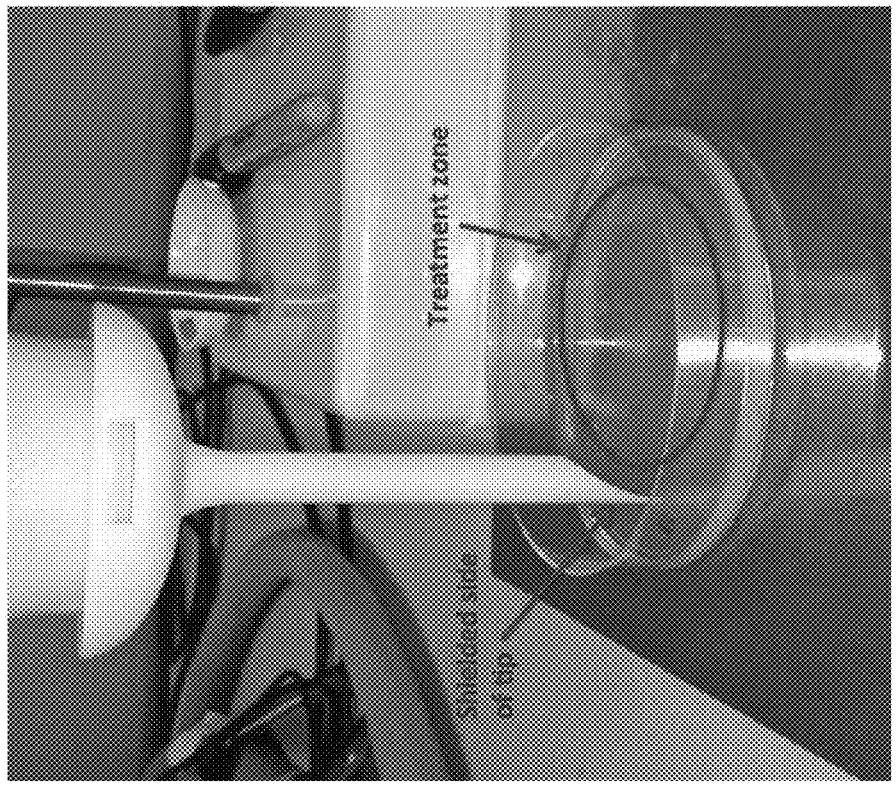

FIGS. 16(*a*) and 16(*b*) illustrate the shielding effect of an exemplary nozzle, in accordance with an embodiment of the present invention.

Figure 17:
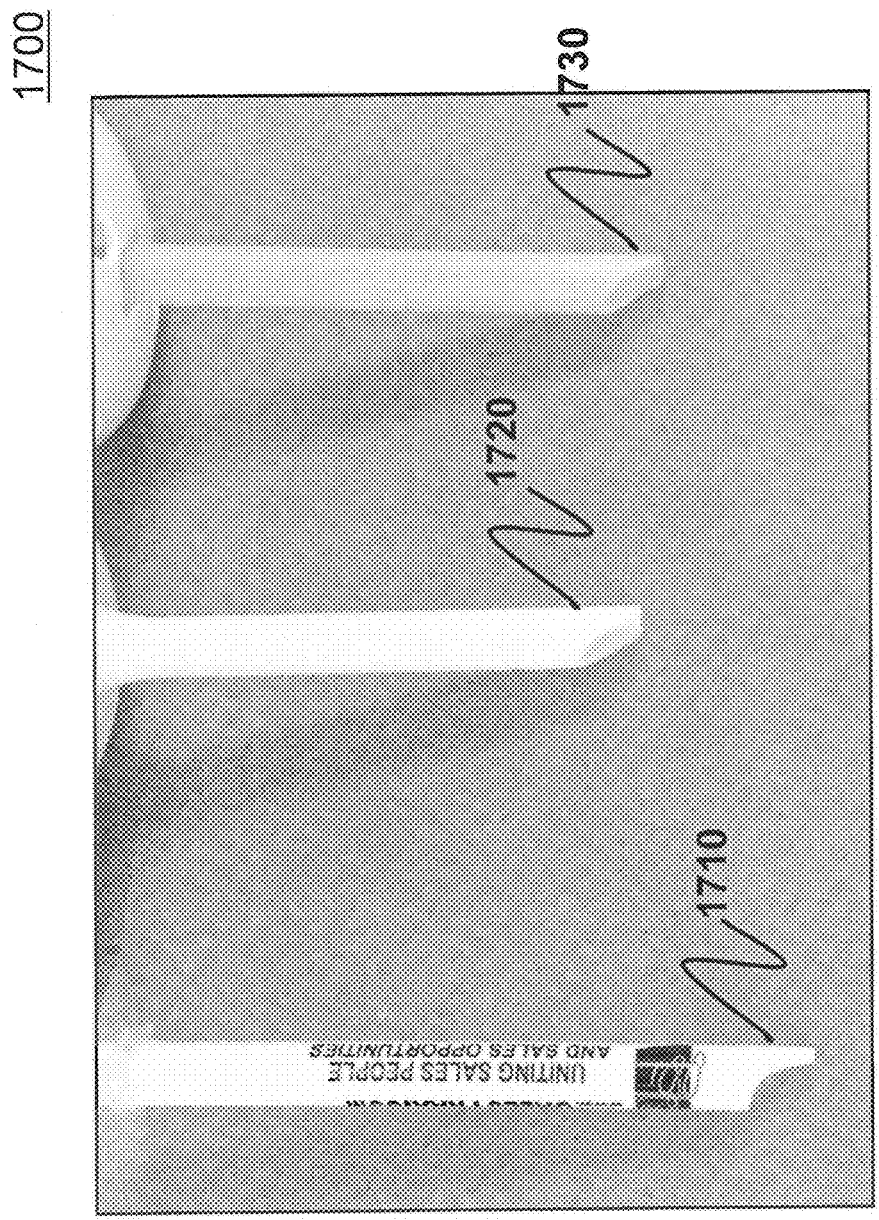

FIG. 17 illustrates exemplary nozzles made from different materials and having different aperture shapes, in accordance with an embodiment of the present invention.

Figure 18:
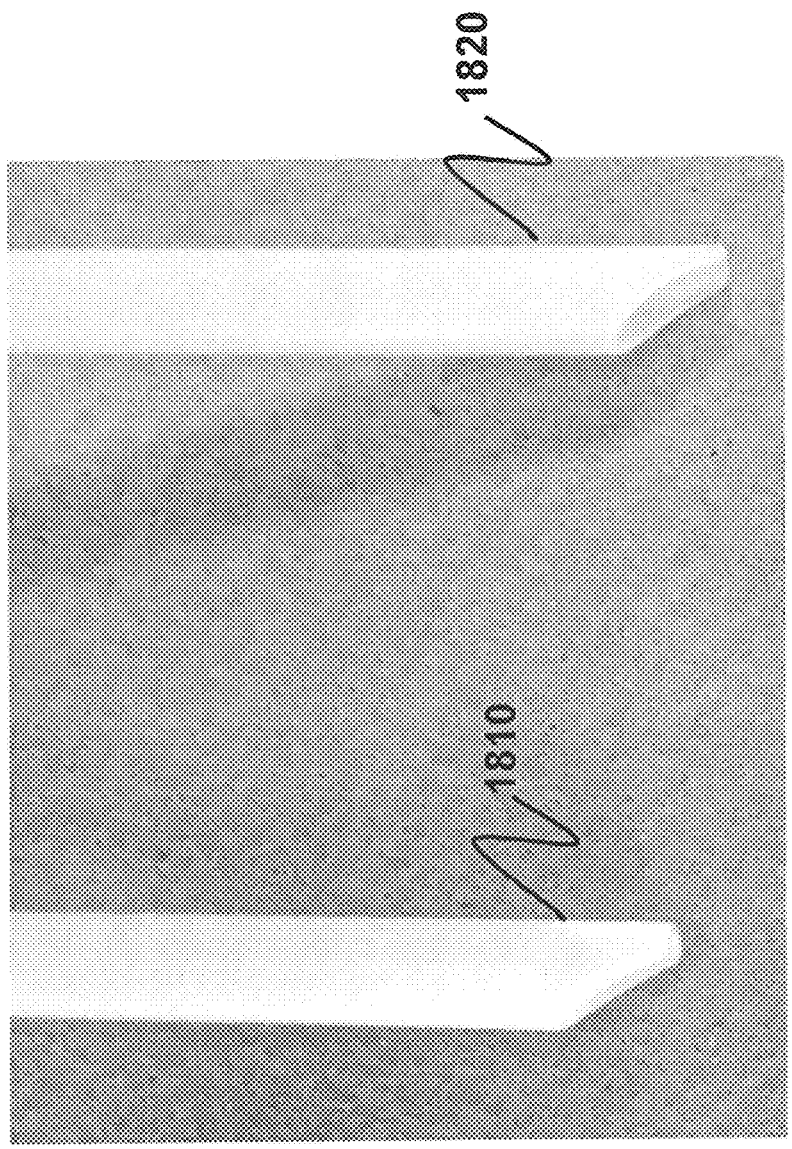

FIG. 18 illustrates exemplary nozzles made from different materials and having different aperture shapes, in accordance with an embodiment of the present invention.

Figure 19:
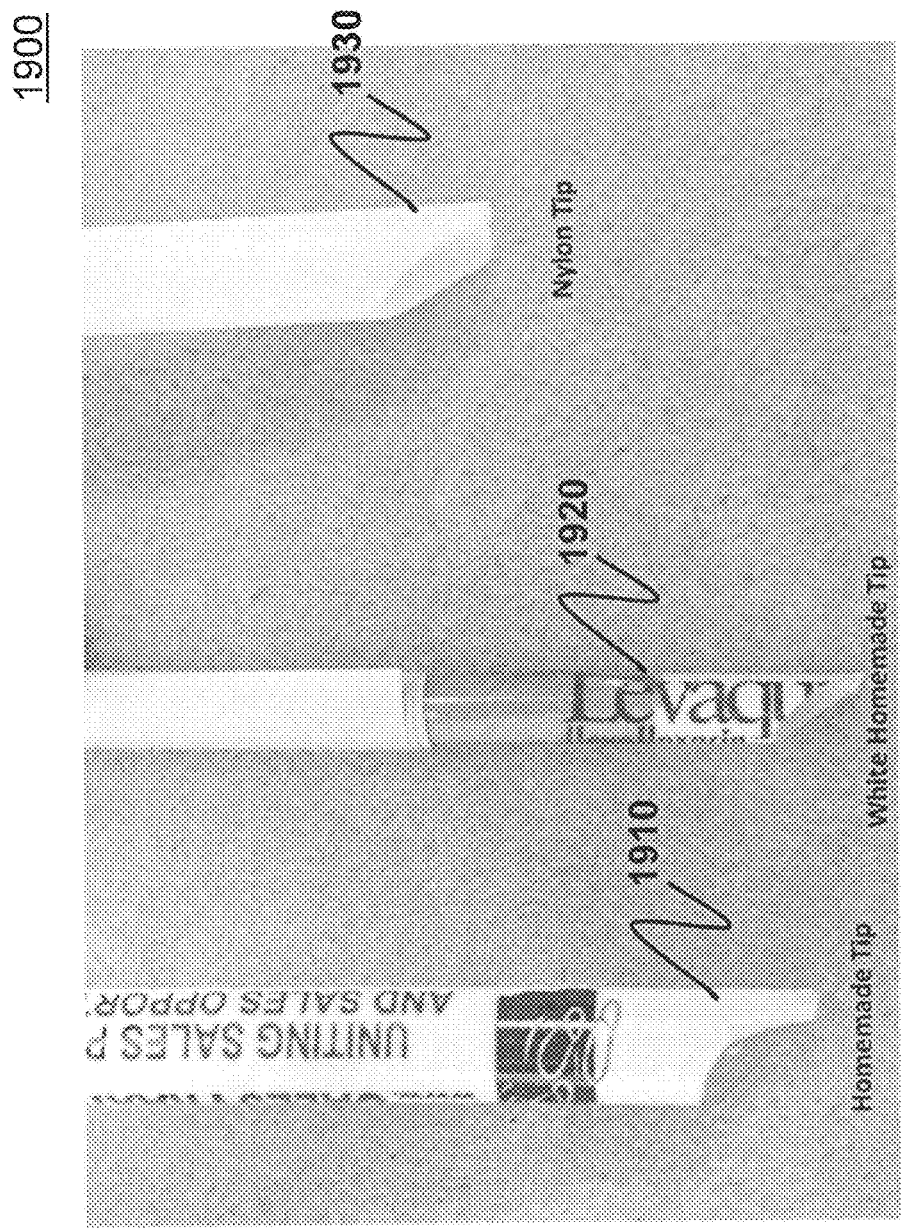

FIG. 19 illustrates exemplary nozzles made from different materials and having different aperture shapes, in accordance with an embodiment of the present invention.

Figure 20:
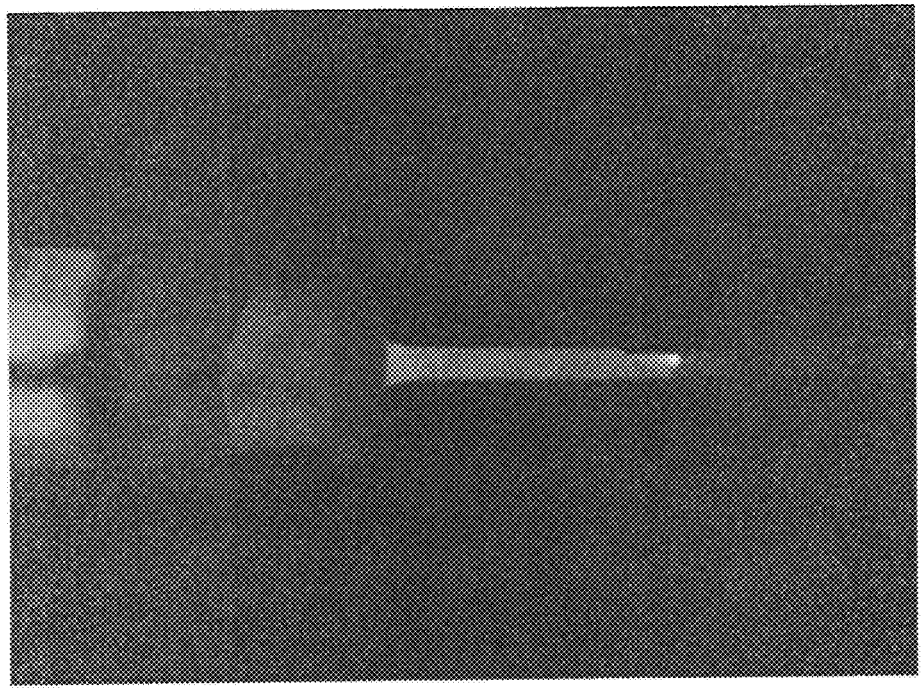

FIG. 20 illustrates the directionality and shielding effect of a nozzle, in accordance with an embodiment of the present invention.

Figure 21B:
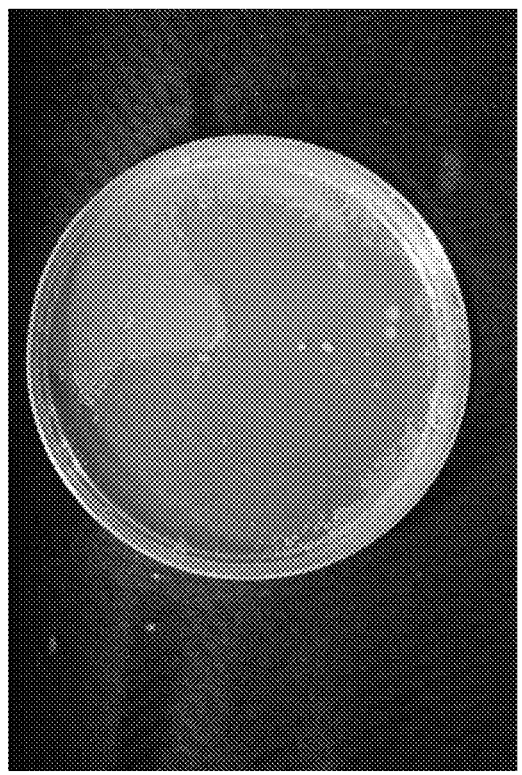
Figure 21A:
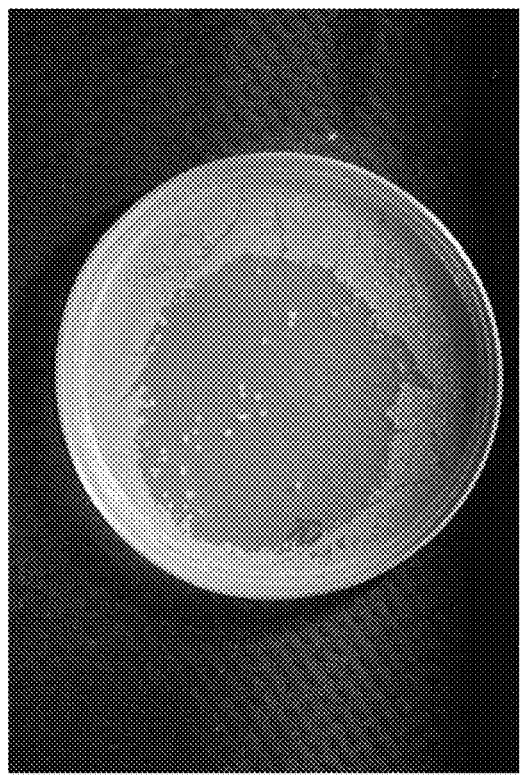

FIGS. 21(*a*) and 21(*b*) illustrate the shielding effects of an exemplary nozzle compared to another nozzle, in accordance with an embodiment of the present invention.

DETAILED DESCRIPTION OF THE INVENTION

Cold temperature atmospheric pressure plasmas have attracted a great deal of enthusiasm and interest by virtue of their provision of plasmas at relatively low gas temperatures. The provision of a plasma at such a temperature is of interest to a variety of applications, including wound healing, anti-bacterial processes, various other medical therapies and sterilization.

Cold Plasma Application Device

Figure 1A:
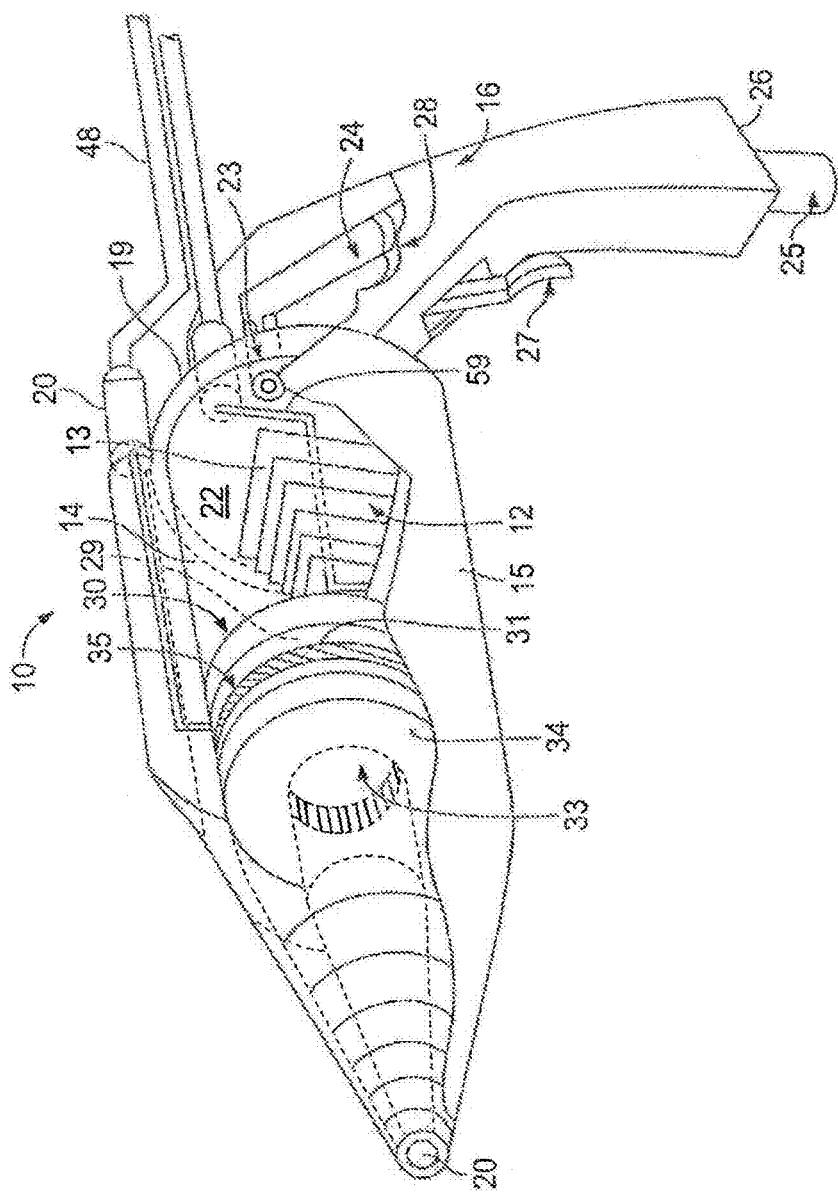
FIGS. 1A and 1B are cutaway views of the hand-held atmospheric harmonic cold plasma device, in accordance with embodiments of the present invention.

To achieve a cold plasma, a cold plasma device typically takes as input a source of appropriate gas and a source of high voltage electrical energy, and outputs a plasma plume. FIG. 1A illustrates such a cold plasma device. Previous work by the inventors in this research area has been described in U.S. Provisional Patent Application No. 60/913,369, U.S. Non-provisional application Ser. No. 12/038,159 (that has issued as U.S. Pat. No. 7,633,231) and the subsequent continuation applications (collectively "the '369 application family"). The following paragraphs discuss further the subject matter from this application family further, as well as additional developments in this field.

The '369 application family describes a cold plasma device that is supplied with helium gas, connected to a high voltage energy source, and which results in the output of a cold plasma. The temperature of the cold plasma is approximately 65-120 degrees F. (preferably 65-99 degrees F.), and details of the electrode, induction grid and magnet structures are described. The voltage waveforms in the device are illustrated at a typical operating point in '369 application family.

Figure 1B:
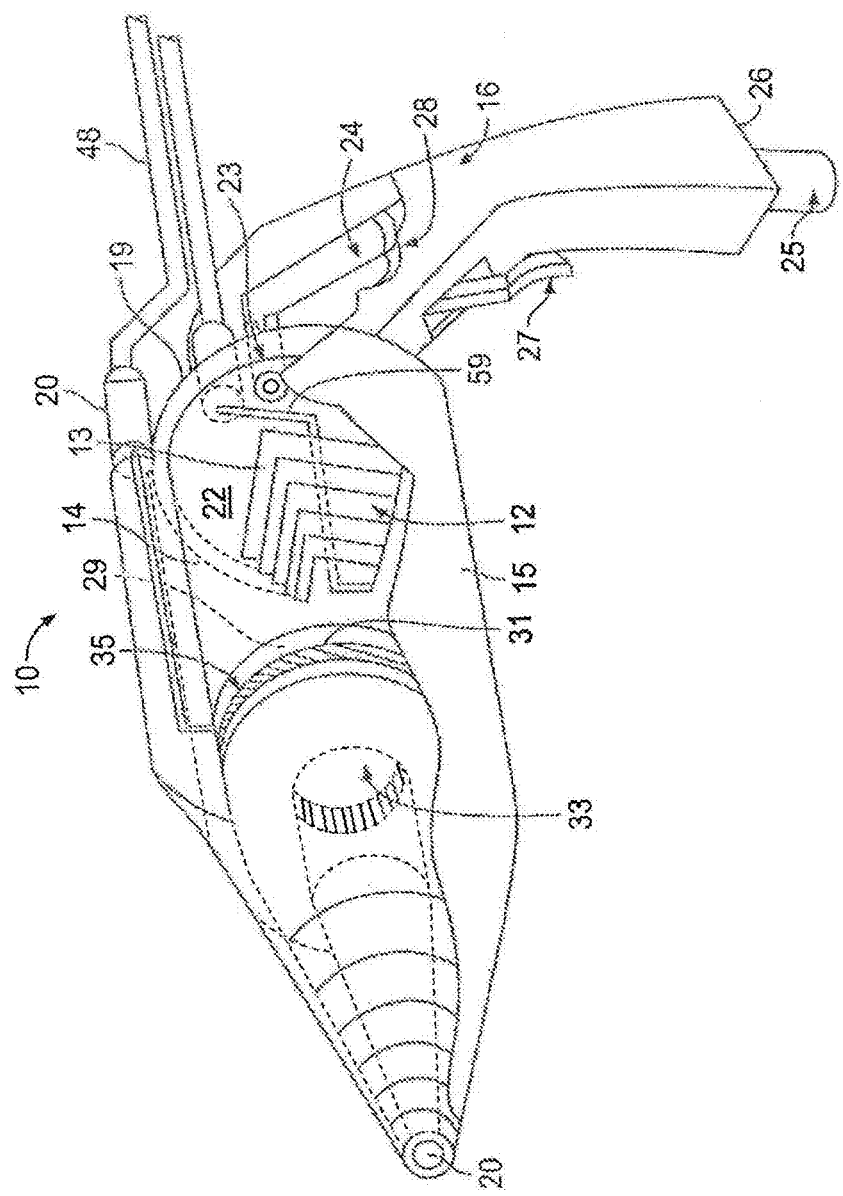
Figure 2A:
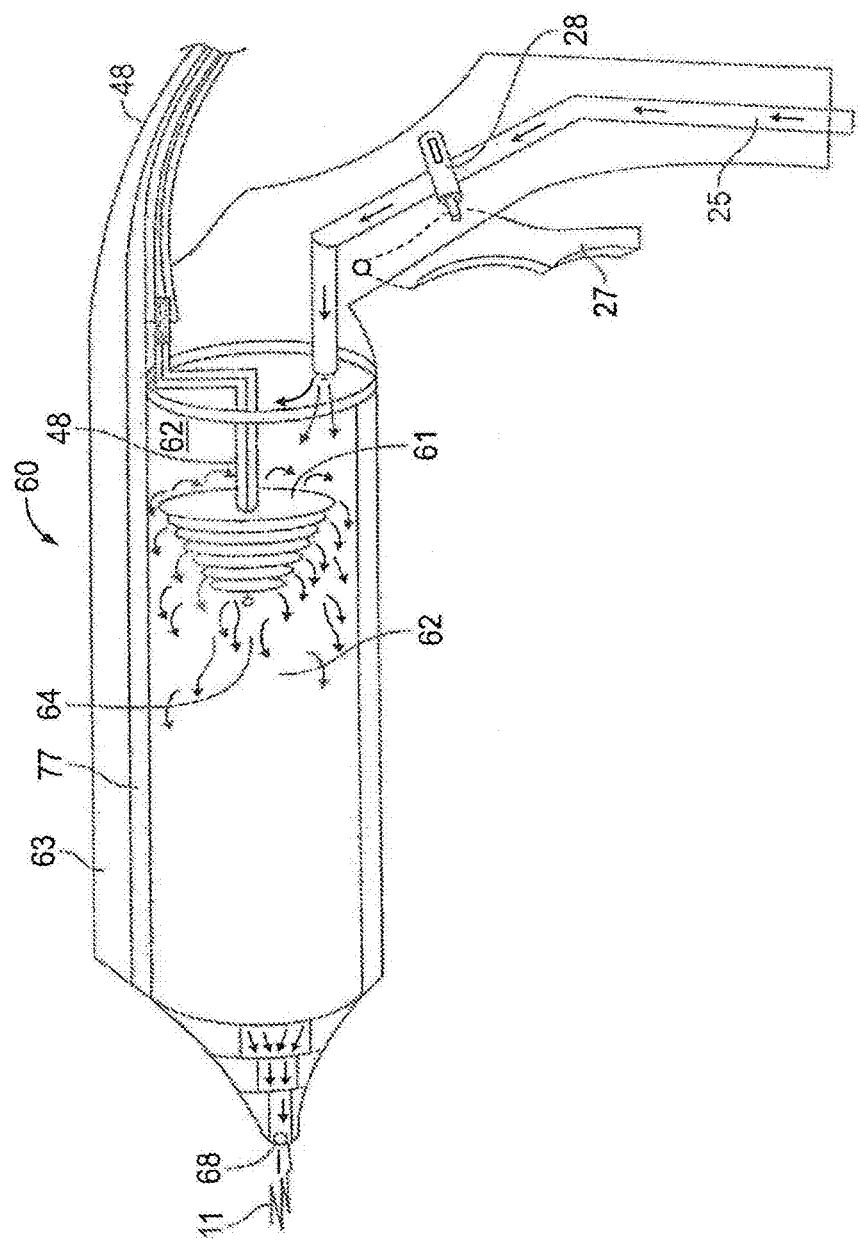
FIGS. 2A and 2B illustrate an embodiment of the cold plasma device without magnets, in accordance with embodiments of the present invention.
Figure 2B:
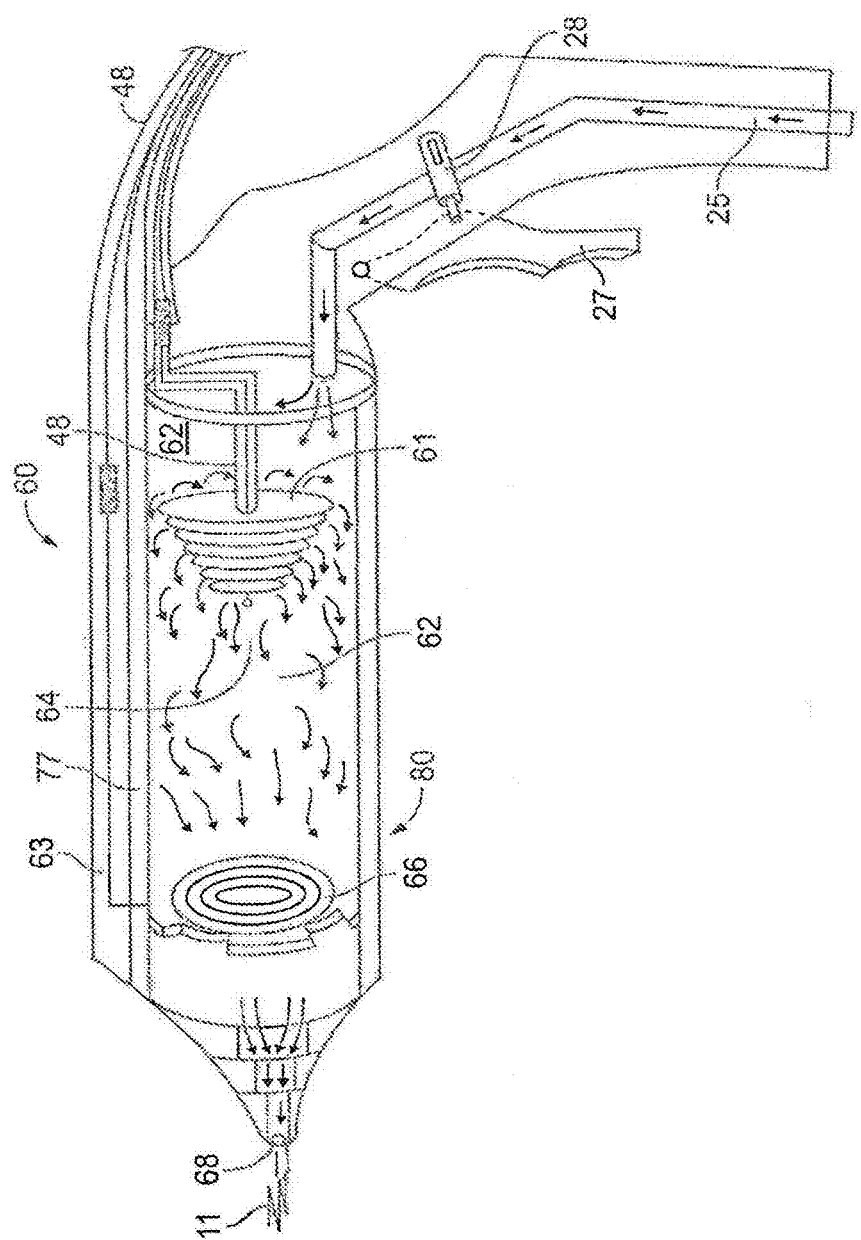

In a further embodiment to that described in the '369 application, plasma is generated using an apparatus without magnets, as illustrated in FIGS. 2A and 2B. In this magnet-free environment, the plasma generated by the action of the electrodes 61 is carried with the fluid flow downstream towards the nozzle 68. FIG. 2A illustrates a magnet-free embodiment in which no induction grid is used. FIG. 2B illustrates a magnet-free embodiment in which induction grid 66 is used. FIG. 1B illustrates the same embodiment as illustrated FIG. 2B, but from a different view. Although these embodiments illustrate the cold plasma is generated from electrode 12, other embodiments do not power the cold plasma device using electrode 12, but instead power the cold plasma device using induction grid 66.

In both a magnet and a magnet-free embodiment, the inductance grid 66 is optional. When inductance grid 66 is present, it provides ionization energy to the gas as the gas passes by. Thus, although the inductance grid 66 is optional, its presence enriches the resulting plasma.

As noted above, the inductance grid 66 is optional. When absent, the plasma will nevertheless transit the cold plasma device and exit at the nozzle 68, although in this case, there will be no additional ionization energy supplied to the gas as it transits the latter stage of the cold plasma device.

As noted with respect to other embodiments, magnetic fields can be used in conjunction with the production of cold plasmas. Where present, magnetic fields act, at least at some level, to constrain the plasma and to guide it through the device. In general, electrically charged particles tend to move along magnetic field lines in spiral trajectories. As noted elsewhere, other embodiments can comprise magnets configured and arranged to produce various magnetic field configurations to suit various design considerations. For example, in one embodiment as described in the previously filed '369 application family, a pair of magnets may be configured to give rise to magnetic fields with opposing directions that act to confine the plasma near the inductance grid.

Cold Plasma Unipolar High Voltage Power Supply

The '369 application family also illustrates an embodiment of the unipolar high voltage power supply architecture and components used therein. The circuit architecture is reproduced here as FIG. 3, and this universal power unit provides electrical power for a variety of embodiments described further below. The architecture of this universal power unit includes a low voltage timer, followed by a preamplifier that feeds a lower step-up voltage transformer. The lower step-up voltage transformer in turn feeds a high frequency resonant inductor-capacitor (LC) circuit that is input to an upper step-up voltage transformer. The output of the upper step-up voltage transformer provides the output from the unipolar high voltage power supply.

Figure 3:
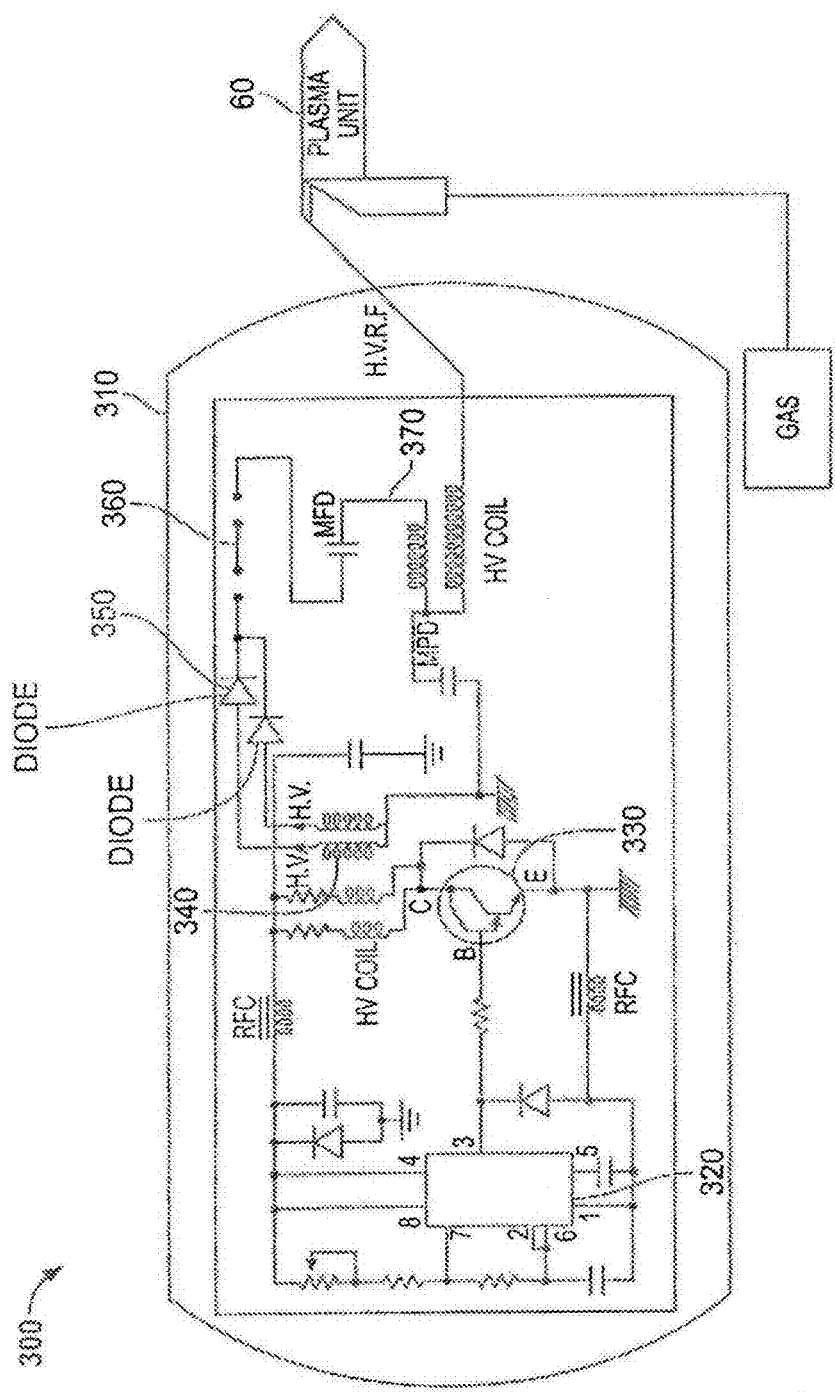
FIG. 3 is an exemplary circuit diagram of the power supply of a cold plasma device, in accordance with embodiments of the present invention.

FIG. 3 also illustrates an exemplary implementation of the unipolar high voltage power supply 310 architecture. In this implementation, a timer integrated circuit such as a 555 timer 320 provides a low voltage pulsed source with a frequency that is tunable over a frequency range centered at approximately 1 kHz. The output of the 555 timer 320 is fed into a preamplifier that is formed from a common emitter bipolar transistor 330 whose load is the primary winding of the lower step-up voltage transformer 340. The collector voltage of the transistor forms the output voltage that is input into the lower step-up voltage transformer. The lower step-up transformer provides a magnification of the voltage to the secondary windings. In turn, the output voltage of the lower step-up voltage transformer is forwarded to a series combination of a high voltage rectifier diode 350, a quenching gap 360 and finally to a series LC resonant circuit 370. As the voltage waveform rises, the rectifier diode conducts, but the quench gap voltage will not have exceeded its breakdown voltage. Accordingly, the quench gap is an open circuit, and therefore the capacitor in the series LC resonant circuit will charge up. Eventually, as the input voltage waveform increases, the voltage across the quench gap exceeds its breakdown voltage, and it arcs over and becomes a short circuit. At this time, the capacitor stops charging and begins to discharge. The energy stored in the capacitor is discharged via the tank circuit formed by the series LC connection.

Continuing to refer to FIG. 3, the inductor also forms the primary winding of the upper step-up voltage transformer 340. Thus, the voltage across the inductor of the LC circuit will resonate at the resonant frequency of the LC circuit 370, and in turn will be further stepped-up at the secondary winding of the upper step-up voltage transformer. The resonant frequency of the LC circuit 370 can be set to in the high kHz-low MHz range. The voltage at the secondary winding of the upper step-up transformer is connected to the output of the power supply unit for delivery to the cold plasma device. The typical output voltage is in the 10-150 kV voltage range. Thus, voltage pulses having a frequency in the high kHz-low MHz range can be generated with an adjustable repetition frequency in the 1 kHz range. The output waveform is shaped similar to the acoustic waveform generated by an impulse such as when a bell is struck with a hammer. Here, the impulse is provided when the spark gap or a silicon controlled rectifier (SCR) fires and produces the voltage pulse which causes the resonant circuits in the primary and secondary sides of the transformer to resonate at their specific resonant frequencies. The resonant frequencies of the primary and the secondary windings are different. As a result, the two signals mix and produce the unique 'harmonic' waveform seen in the transformer output. The net result of the unipolar high voltage power supply is the production of a high voltage waveform with a novel "electrical signature," which when combined with a noble gas or other suitable gas, produces a unique harmonic cold plasma that provides advantageous results in wound healing, bacterial removal and other applications.

The quenching gap 360 is a component of the unipolar high voltage power supply 310. It modulates the push/pull of electrical energy between the capacitance banks, with the resulting generation of electrical energy that is rich in harmonic content. The quenching gap can be accomplished in a number of different ways, including a sealed spark gap and an unsealed spark gap. The sealed spark gap is not adjustable, while unsealed spark gaps can be adjustable. A sealed spark gap can be realized using, for example, a DECI-ARC 3000 V gas tube from Reynolds Industries, Inc. Adjustable spark gaps provide the opportunity to adjust the output of the unipolar high voltage power supply and the intensity of the cold plasma device to which it is connected.

In a further embodiment of the present invention that incorporates a sealed (and therefore non-adjustable) spark gap, thereby ensuring a stable plasma intensity.

In an exemplary embodiment of the unipolar high voltage power supply, a 555 timer 320 is used to provide a pulse repetition frequency of approximately 150-600 Hz. As discussed above, the unipolar high voltage power supply produces a series of spark gap discharge pulses based on the pulse repetition frequency. The spark gap discharge pulses have a very narrow pulse width due to the extremely rapid discharge of capacitive stored energy across the spark gap. Initial assessments of the pulse width of the spark gap discharge pulses indicate that the pulse width is approximately 1 nsec. The spark gap discharge pulse train can be described or modeled as a filtered pulse train. In particular, a simple resistor-inductor-capacitor (RLC) filter can be used to model the capacitor, high voltage coil and series resistance of the unipolar high voltage power supply. In one embodiment of the invention, the spark gap discharge pulse train can be modeled as a simple modeled RLC frequency response centered in the range of around 100 MHz. Based on the pulse repetition frequency of 192 Hz, straightforward signal analysis indicates that there would be approximately 2,000,000 individual harmonic components between DC and 400 MHz.

In another embodiment of the unipolar high voltage power supply described above, a 556 timer or any timer circuit can be used in place of the 555 timer 320. In comparison with the 555 timer, the 556 timer provides a wider frequency tuning range that results in greater stability and improved cadence of the unipolar high voltage power supply when used in conjunction with the cold plasma device.

Cold Plasma Plumes

The unique harmonic cold plasma resulting from the novel "electronic signature" of the power supply applied with an appropriate noble gas combination can be used with a variety of shaped cold plasma plumes or jets. In fact, various medical treatments can require differing shaped plasma plume shapes. For example, medical treatments involving dermatology applications, skin cancer, dental caries, very small wounds and the like are desirous of a relatively small confined cold plasma plume shape. In fact, for the mentioned applications, the preferred plasma plume shape is one having a very small diameter coverage area. In such applications, a circular, pinpoint plasma jet is a preferred plume shape. Similarly, other medical treatments can require a narrow and broad plasma jet. For example, medical treatments involving surgical site applications, diabetic ulcers, large wounds and the like are desirous of a relatively narrow but long cold plasma plume shape. In such applications, a slit-shaped plasma jet is a preferred plume shape.

Similarly, other medical treatments can require a wide and long plasma jet. For example, medical treatments involving certain other surgical site applications, and certain shapes of large wounds and the like are desirous of a relatively wide and long cold plasma plume shape. In such applications, a spatula-shaped plasma jet is a preferred plume shape.

Not all medical treatment protocols are associated with treatment sites external to the body of a human or animal. In many cases, the treatment site is internal to a body and a cold plasma treatment protocol would therefore require delivery of cold plasma to that internal treatment site. Access to such a site can use various elongated devices, such as laparoscopic, arthroscopic and endoscopic devices. Cold plasma is generated by a device such as the cold plasma application device described above, and introduced into the proximal end of one of these elongated devices, with delivery of cold plasma at the distal end. Accordingly, the gas (helium or other biocompatible gas/gas mixture) is delivered to the desired treatment site, together with the electrical energy to ignite the desired reactive species, as well as any energy delivery required for RF or electroporation protocols.

Different configurations of a nozzle connected to the cold plasma device result in different plasma flow pattern shapes and these plasma flow pattern shapes can be optimized for various applications. Thus, for example, burns covering a wide area are optimally treated by a nozzle that supports a cold plasma with a wide cross-sectional area. Conversely, a small but deep wound or an internal injury is optimally treated by the use of a nozzle connected to the cold plasma device to support a plasma flow pattern shaped in a small circular cross-section. Other wound shapes can be optimally treated with a variety of other nozzles to support the required shapes such as a slit shape.

While such different plasma flow patterns require a different nozzle shape, nozzle shapes cannot be arbitrarily shaped without adverse impact on the cold plasma. In particular, the temperature and stability of the cold plasma can be adversely affected by modest changes in the nozzle configuration. In fact, the temperature and stability of the cold plasma are the function of a complex relationship between such characteristics as gas flow rate, electrode configuration, electrical power waveform, nozzle configuration and gap between target surface and nozzle. Therefore, a method to recognize the nozzle attached and adjust these parameters (e.g. voltage, frequency, gas flow) is highly desired, and is addressed below.

For medical devices that come into proximate or direct contact with patients, the devices must be sterilized between uses or contain disposable components designed to reduce or eliminate the transfer of infection between patients. While sterilization may appear to be more efficient, sterilization takes specialized equipment, specially trained staff, and additional time and resources. Even with these people and processes, the reprocessing of medical equipment can still be a source of infection. Furthermore, certain medical electronics or other complex hardware cannot tolerate the extreme temperatures, pressures, or chemical stresses of sanitization. For these reasons, disposable components are increasingly common in modern healthcare delivery. These disposables are well known in the medical industry and range in form and complexity from a simple disposable tube on the suction device at a dental office to a fully customized, patient-specific, cutting guide used by an orthopedic surgeon when performing total knee replacement surgery.

When treating open wounds with an instrument such as cold plasma, it is important to ensure that no new pathogens are introduced to the wound and that pathogens are not spread from patient to patient. Therefore, it is desirable to have a sterile, prepackaged, and easily exchangeable delivery tip that can be disposed of and replaced between each use. Further, the different size, shape, and complexity of different wounds may warrant a different size or shape to the plasma plume for a patient-specific approach to plasma wound therapy. The following embodiments seek to meet these needs with disposable plasma nozzles capable of generating and supporting unique and varied plasma plume shapes.

Cold Plasma Nozzles

Figure 4A:
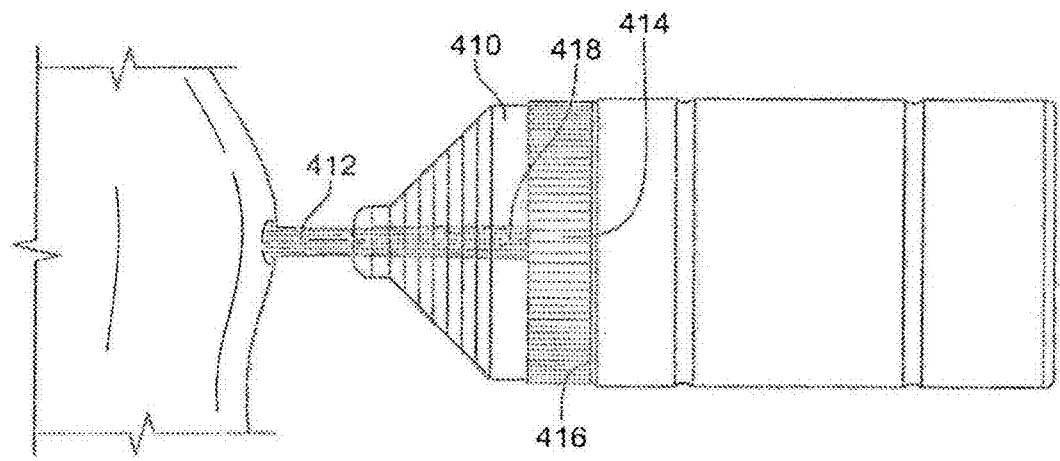
FIGS. 4A and 4B illustrate a number of exemplary aperture shapes of cold plasma device nozzles, in accordance with embodiments of the present invention.
Figure 4B:
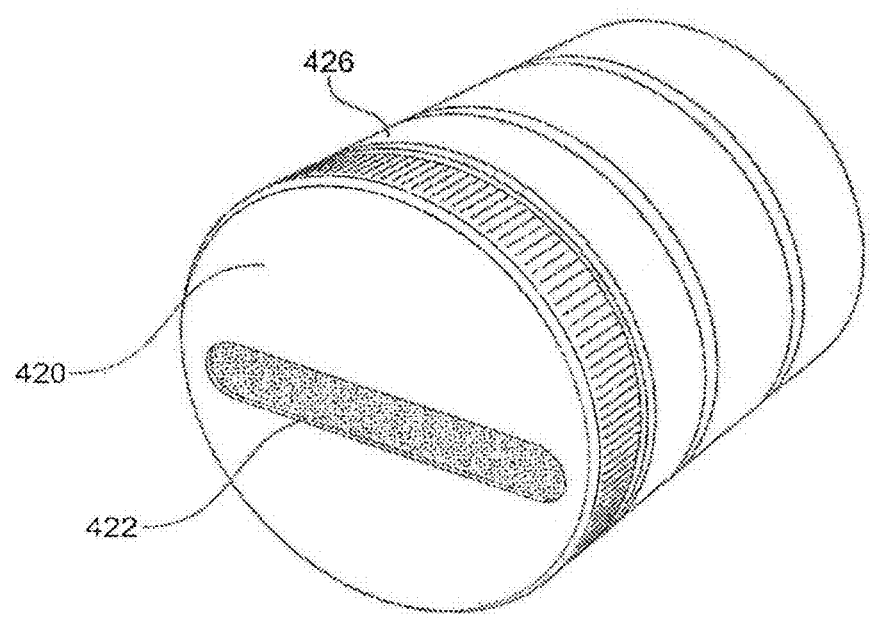

FIG. 4 illustrates different nozzles 410, 420 that can be affixed to the outlet port of the cold plasma device. These nozzles represent examples of different orifice shapes and sizes 412, 422, and are not intended to be limiting to the scope of the invention. The illustrated nozzles 410, 420 include circular and slit shaped apertures. Other shapes are included in the scope of embodiments of the present invention, e.g., triangular shaped apertures. By way of example, and not as a limit to the scope of the invention, the circular orifice can be 3, 5, 8, and 42 mm in diameter. The 42 mm diameter orifice, being a larger orifice size, requires additional elements to support such a large plume, as discussed further below. Nozzles having a circular aperture produce essentially a conico-cylindrical plasma plume.

As noted above, other aperture shapes fall within the scope of the present invention. In particular, shapes configured to support plume coverage areas such as square, oval, triangle, and the like fall within the scope of the present invention. To the extent that certain treatment areas having a non-standard shape demand a cold plasma plume having a complementary shape, an adaptable nozzle also falls within the scope of the present invention. An adaptable nozzle uses either a mechanical adjustment or is formed from a malleable material having sufficient limited range of dimensional adjustments such that the orifice or aperture shape can be modified. The limited range of dimensional adjustment is designed to maintain a back pressure that remains within the range sufficient to support and maintain the cold plasma plume.

As discussed above, nozzles are attached to the outlet of the cold plasma device to provide a plasma plume comparable to that of the '369 patent, but with differing coverage areas and/or shapes. Such nozzles can be permanently affixed to the cold plasma device. In an alternative set of embodiments, such nozzles can also be detachably affixed to the cold plasma device. Means of affixing the detachable plasma nozzles include threaded screw assembly, squeeze fit, clamps, spring loaded locking collar and other attachment means that one of ordinary skill in the art would have familiarity. Detachable nozzles can be reusable nozzles, in that these nozzles can be used on more than one occasion. In a set of further embodiments, the detachable nozzles can be disposable nozzles, in that the nozzles are used once and then discarded. With removable/disposable plasma nozzles, it can be desirable to have a dust/debris cover over the outflow port when the cold plasma device is not in use.

Figure 5:
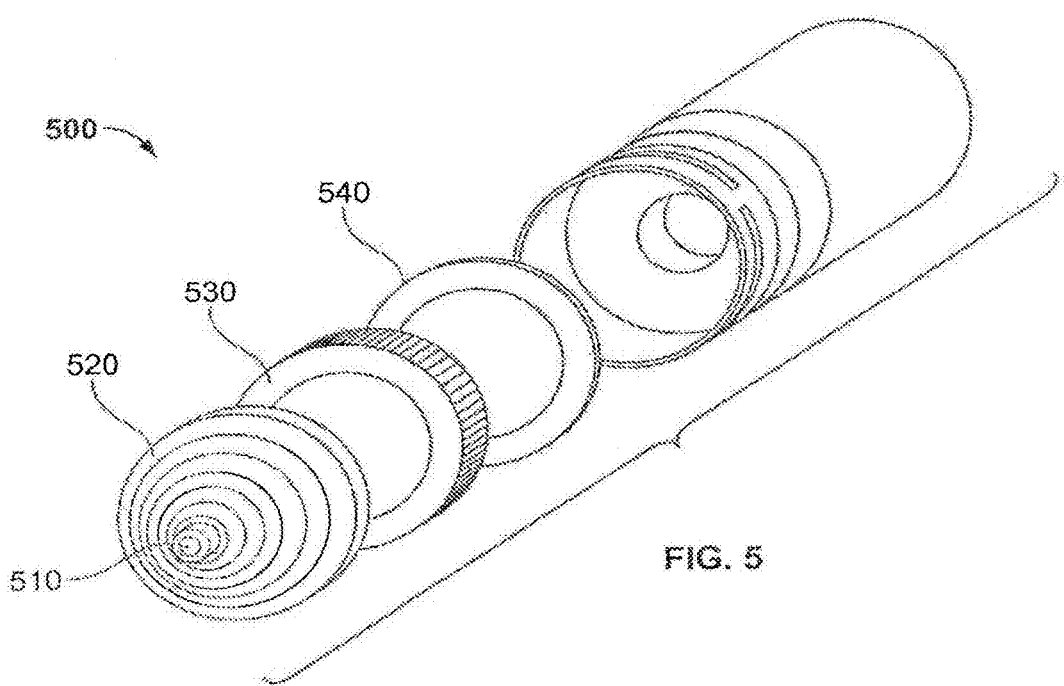
FIG. 5 illustrates an exemplary nozzle assembly for a cold plasma device, in accordance with an embodiment of the present invention.

FIG. 5 illustrates an exemplary nozzle assembly for a cold plasma device, in accordance with an embodiment of the present invention. The exemplary nozzle assembly 500 includes distal orifice 510 in an acrylic section 520, a polypropylene distal cap 530, and silicon spacer 540. Silicon spacer 540 makes contact with cold plasma device. The particular parts shown in the assembly are merely exemplary, as are the choice of materials, and other choices for coupling a nozzle to a cold plasma device fall within the scope of embodiments of the present invention.

In a further embodiment of the present invention, a nozzle can include more than one aperture. For example, embodiments of the present invention can include a nozzle with a plurality of small apertures in it, similar to a salt shaker, in order to achieve multiple smaller parallel plasma streams (not pictured).

As noted above, nozzle apertures cannot be of arbitrary dimensions yet still sustain a cold plasma plume. For example, a nozzle aperture cannot be arbitrarily increased without loss of a stable cold plasma plume. To support a large nozzle aperture (e.g. a large circular or oval orifice, a large slit aperture) and its resulting large coverage area, an additional material and construction step are required to effectively distribute the cold plasma over the larger area while maintaining a smooth and well-formed plasma plume.

Figure 6:
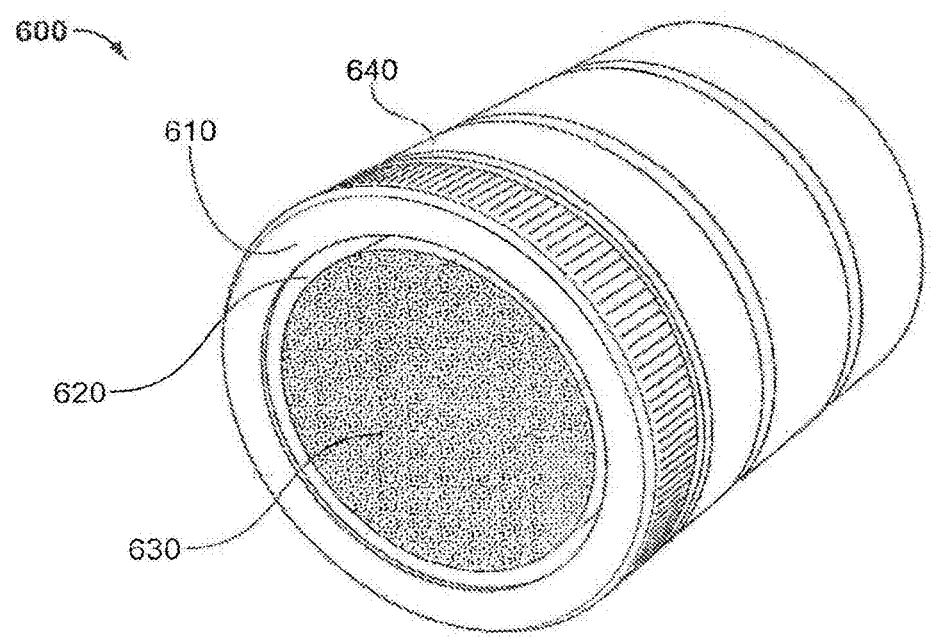
FIG. 6 illustrates an exemplary nozzle having a plurality of sub-apertures within the body length of the nozzle, in accordance with an embodiment of the present invention.

In an embodiment of the present invention, as illustrated in FIG. 6, a porous material can be added in the form of a disk 630 for a portion of the body length between proximal aperture 620 and distal aperture 640 of the nozzle 610. The porous material extends across the complete cross-section of the nozzle 610, and thereby provides a plurality of small sub-apertures through which the cold plasma travels. The thickness of the porous material, as well as its porous nature, provide sufficient backpressure to sustain the cold plasma plume. The use of a porous material forces the cold plasma to travel through the pore structure of the foam while providing adequate backpressure into the plasma generation chamber in the presence of such a large outflow from the large orifice of the nozzle. Some backpressure is necessary to ensure sufficient contact time between the feed gas and the RF structure for ionization to occur. The porous material can be any suitable material consistent with the above objectives. In an exemplary embodiment, the porous material can be an open cell polyurethane foam. Consistent with the above objectives, the polyurethane foam provides a very large, almost infinite, plurality of sub-apertures. The use of porous material has led to cold plasma plumes that are orders of magnitude larger than previously seen. In an exemplary embodiment, a cold plasma plume of 42 mm diameter can be created. In an embodiment, the porous material (e.g., foam disk) can be located anywhere along the cold plasma path from the gun through to the disposable tip. The porous material (e.g., foam disk) would be affixed to maintain its position at its desired location so that it is not amenable to being dislodged in response to the cold plasma flow. In an exemplary embodiment, the foam disk can be located (i.e., sandwiched) between the disposable tip and the body of the gun. Although disk 630 is shown as a cylindrical shape, the shape will be consistent with the shape of the apertures 620, 630. Thus, for example, in the case of slit-shaped apertures, disk 630 can take on a shape having a rectangular cross-section. Alternatively, a single generic shape (e.g., cylindrical disk shape) can be used with a variety of different aperture cross-sections, with only the portion presented to the aperture cross-section being active. For example, a cylindrical disk shape can be used with a slit aperture, with only the slit portion of the cylindrical disk being actively exposed to the cold plasma.

In a further embodiment, the inclusion of this porous material (e.g., polyurethane foam) provides the potential for delivering additional chemicals or drugs along with the cold plasma plume. For example, the foam could come presoaked in any number of solutions such as water, saline solution, hydrogen peroxide, or powders (e.g., powdered medications such as bleomycin, collagenase, and the like). The first two solutions could be used to humidify the plasma, which has been shown to enhance the antimicrobial action of certain cold plasmas. The third solution can enhance the oxidative potential of the cold plasma to enhance antimicrobial action or otherwise control the chemistry of the cold plasma. It may also be desirable to include antibiotic solutions or other medication, such as haemostatic agents, anesthetics, for the enhanced control of infection, bleeding, and pain from the target wound.

Cold Plasma Cannula Tubes

As noted above, not all medical treatments can be performed external to the body of a human or animal. In many cases, the treatment site is internal to a body and access to such a site requires the provision of tools that are placed at the end of various elongated devices, such as laparoscopic, arthroscopic and endoscopic devices. In another embodiment of the present invention, the nozzle can be a cannula tube attached to the outlet port of the cold plasma device. FIG. 7 illustrates an exemplary cannula tube 710. In an exemplary embodiment, cannula tube 710 has a single aperture 720 at the proximal end that is attached to the outlet port of the cold plasma device. Cannula tube 710 has a length sufficient to reach a desired treatment area. Typically, the treatment area is internal to a human being or animal, where the treatment area is accessible via an opening such as mouth, nose, arterial or venal entry point, or transdermally through a port. Thus, a cannula tube can be used for internal treatment within any bodily lumen, cavum, vestibule or buccal cavity. Similar to the other nozzles, the cannula tube can be either removable or permanently affixed to the cold plasma device. Also in a similar manner to the other nozzles, the cannula tube can be either reusable or disposable cannula tubes. In an embodiment of the present invention, the cannula tube has a single aperture 730 at the distal end inserted into the treatment area. Cannula tube 710 can be used for internal treatment within any bodily lumen, cavum, vestibule, or buccal cavity.

FIG. 8 illustrates a further embodiment of the present invention, a cannula tube 810 has a plurality of apertures 840a, b, c at the distal end of the cannula tube. In various embodiments, the apertures can be at the end or placed at a variety of locations along a portion of the length of the cannula tube adjacent to the end of the cannula tube. In one of these embodiments, the distal end 830 of the cannula tube can be sealed, with one or more apertures 840a, b, c located along the body length. Cannula tube 810 can be used for internal treatment along the length of any bodily lumen, cavum, vestibule, or buccal cavity.

Cold Plasma Shrouds

Figure 9:
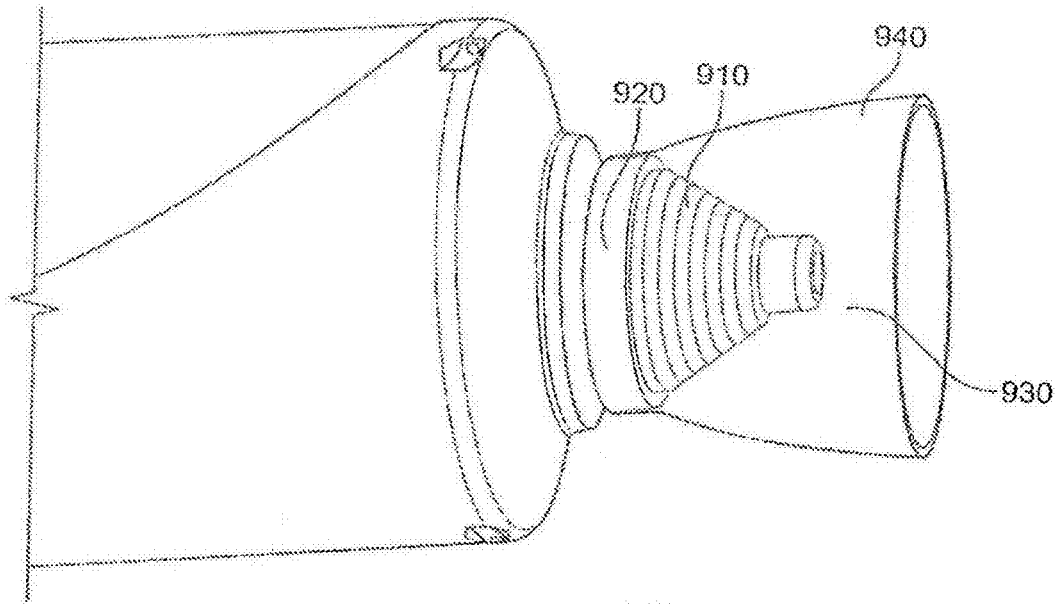
FIG. 9 illustrates an exemplary shroud for use with a nozzle attached to a cold plasma device, in accordance with an embodiment of the present invention.
Figure 10:
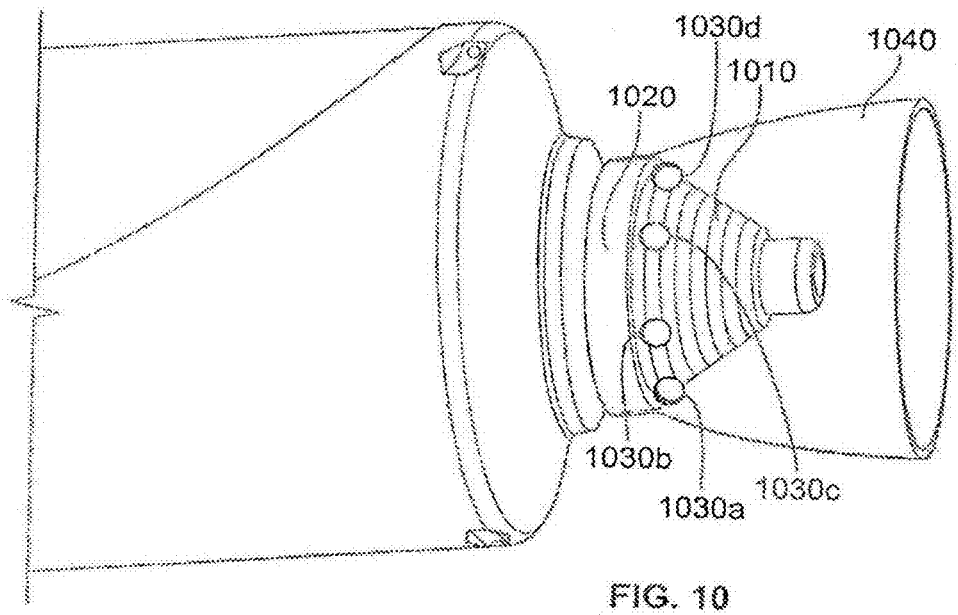
FIG. 10 illustrates an exemplary shroud for use with a nozzle having multiple output apertures, the nozzle attached to a cold plasma device, in accordance with an embodiment of the present invention.

FIG. 9 illustrates a further embodiment of the present invention, a shroud 940 can be placed so as to surround the area occupied by the cold plasma plume. The shroud functions to keep reactive species in closer proximity to the wound bed or target substrate for longer durations of time when reactive species are desired and proper feed gas is used for their production. Additionally, it maintains high energy ions around the target area rather than allowing the energy to escape quickly into the ambient environment. Thus, the shroud separates the external atmosphere from the cold plasma. In one exemplary embodiment, shroud 940 can be cone-shaped, although other shapes fall within the scope of embodiments of the present invention. In another embodiment of the present invention, the shroud could also have one or more outlet apertures 1030 b, c, in the form of narrow elliptical or circular ports, as illustrated in FIG. 10. The outlet apertures enable gas flow to be maintained when the shroud is pressed against skin or another substrate by providing an exit path for the cold plasma. In other words, the outlet apertures allow fluid communication between the external atmosphere and the cold plasma inside the shroud. The outlet apertures can be located anywhere on the shroud. In one embodiment, the outlet apertures can be located proximal to the gun to ensure that the energy-rich plasma is maintained at the treatment area, while the quenched cold plasma is released to the external atmosphere.

In addition, the shroud also serves to provide the medical professional with a minimum distance guide, i.e., the nozzle cannot approach the treatment site any closer than that permitted by the shroud. In an embodiment, the length of the shroud can be in the range 10 to 35 mm although shroud lengths as small as 2 mm are within scope of embodiments of the invention. The shroud diameter can also provide the medical professional with an indication of the effective zone of treatment. For example, in an exemplary cold plasma treatment protocol, an 8 mm diameter plasma can be associated with a 55 mm diameter treatment zone. Therefore, a shroud diameter of 55 mm coupled with an 8 mm aperture would indicate to the medical professional that the cold plasma application device would be moved by one-shroud-diameter to reach the next treatment zone. Thus, the choice of shroud dimensions can depend upon the nozzle size, as well as the type of treatment protocol.

As noted above, the shroud may also function to keep the plasma stream and treatment area separate from the surrounding ambient air/environment. This could work to control plasma chemistry, for example when pure helium is used as a feed gas, reactive $O_2$ and $N_2$ species would be minimized as they are normally introduced when the helium plasma stream causes turbulent mixing with ambient air containing $O_2$ and $N_2$ as well as $H_2O$.

Cold Plasma Sterile Sleeves

In a further embodiment of the present invention, nozzles are formed as part of a sterile assembly. A sterile nozzle assembly 1100 provides for the provision of a sterile nozzle that can be coupled to a cold plasma device 1210. The cold plasma device is not a sterile device, and the non-sterile area is separated from the sterile nozzle by a protective element such as a sleeve 1140.

Figure 11:
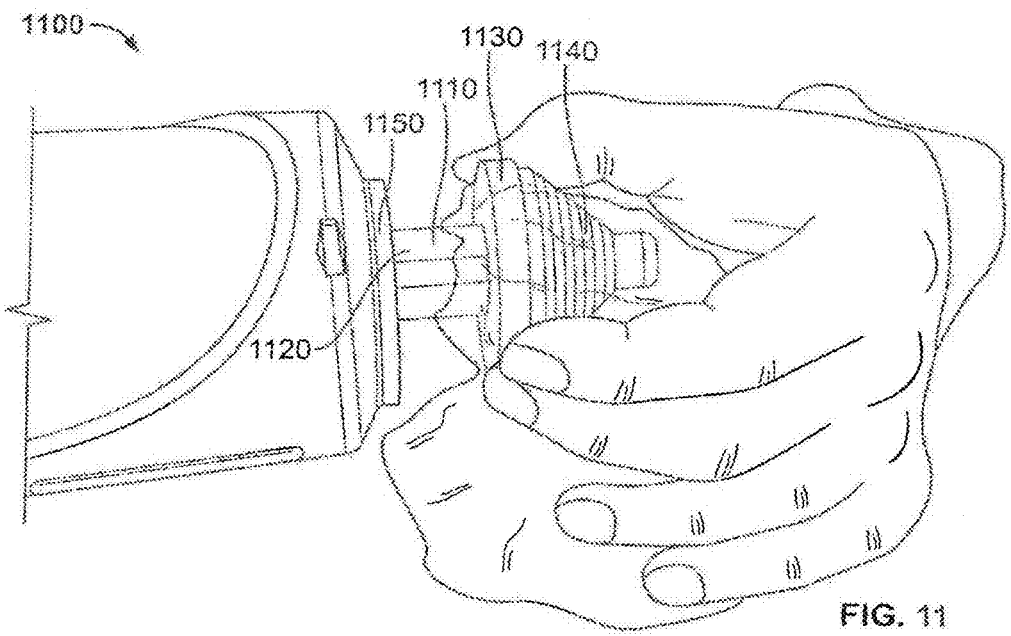
FIG. 11 illustrates an exemplary sterile sleeve enclosing a sterile nozzle for use with a cold plasma device, in accordance with an embodiment of the present invention.

FIG. 11 illustrates a threaded nozzle end 1150 of nozzle 1110 that is incorporated with the sterile sleeve into a single unit for the purposes of handling an insertion. Disposable nozzle 1110 could be RF welded, glued, epoxied, or otherwise permanently attached to the sterile sleeve by any means known to one familiar in the art. In an alternative embodiment, a rubber "O" ring can be used as part of the sterile sleeve, with the rubber "O" ring placed over the threaded portion of the disposable tip. The "O" ring is not permanently attached, but would function as a single unit.

Figure 12:
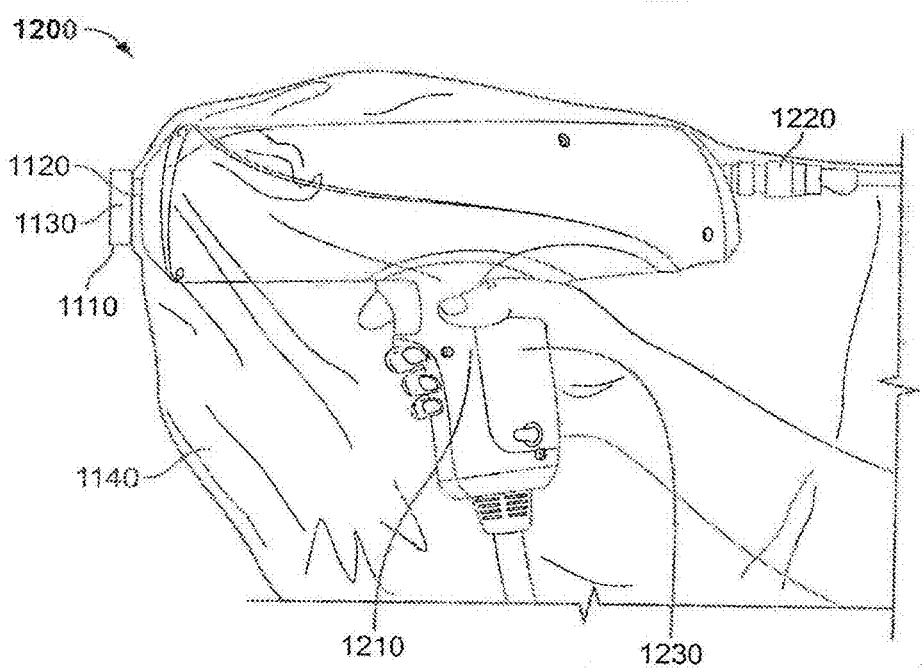
FIG. 12 illustrates an exemplary sterile sleeve in its inverted position, the sterile sleeve now exposing a sterile nozzle for use with a cold plasma device, in accordance with an embodiment of the present invention.

FIG. 12 illustrates the incorporated disposable nozzle 1110 and sterile sleeve 1140 after being pulled over the cold plasma device 1210. Note that the sleeve covers the cold plasma device, the power cord 1220 associated with the cold plasma device, together with anything else that is required to be kept apart from the sterilized aperture of the disposable nozzle, e.g., the hand and distal arm of the medical professional using the cold plasma device and disposable nozzle.

In further embodiments of the cold plasma application device and/or universal power supply, a smart electronics feature can be added. With this feature added to either the cold plasma application device and/or universal power supply, the power supply can recognize the type of cold plasma hand piece that is connected to the power supply, and adjust the power supply output accordingly. For example, with a different hand piece, the output voltage, output resonant frequency or timer frequency can be adjusted to support the particular hand piece being used. In a further embodiment, the smart electronics can recognize not only the particular hand piece being connected to the power supply, but also one or more of the particular plasma nozzles being connected at the gas outlet of the hand piece and the composition of gas and the duration of treatment based on the connection at the gas inlet. Based on being able to sense the plasma-nozzle-hand-piece combination, predetermined settings can be automatically made by the power supply in response to these sensed configurations. The sensing process can be accomplished by any of the numerous methods by which such configuration data can be obtained. For example, the coding of the hand-piece and/or plasma nozzle can be performed via an ID chip (e.g., a RFID chip), which can be read remotely by the appropriate RFID interrogator installed in the power supply or the hand-piece. Other alternative means of information storage include electrically erasable programmable read only memory (EEPROM). Other alternatives for the sensing include the use of simple mechanical-electrical connections such as pin connectors or the use of printed metal stripes (similar to a barcode) on the surface of the plasma nozzle or cartridge that physically makes the desired connection. The configuration data can include the hand-piece-tip configuration, or could also contain information such as safety and other information (such as maximums and minimums) that are set by various regulatory and other authorities. For example, the data memory can indicate the maximum time to which a particular treatment area can be exposed. Where more complex relationships apply to various relevant operating parameters, such information can also be stored in the data memory. In addition to remote sensing of the data memory, wired and/or wireless connectivity can be provided to make the relevant information available to the power supply. In response to the received data, the power supply responds automatically by making the appropriate settings, such as pulse frequency, resonance frequency, output voltage, gas flow rates, and treatment time.

Cold Plasma Methods

Figure 13:
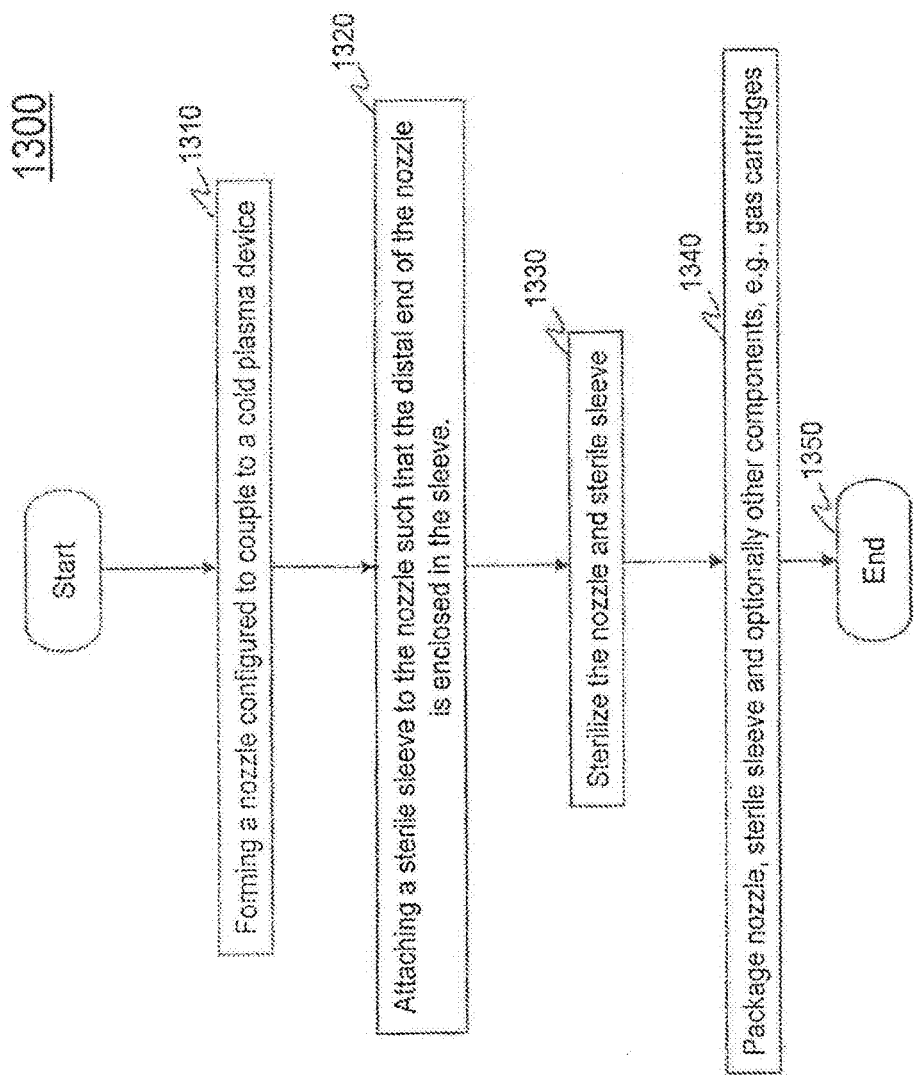
FIG. 13 illustrates a method for manufacturing a nozzle for use with a cold plasma device, in accordance with an embodiment of the present invention.

FIG. 13 provides a flowchart of an exemplary method 1300 to manufacture a sterile nozzle for use with a cold plasma device, according to an embodiment of the present invention.

The process begins at step 1310. In step 1310, a nozzle is formed that is configured to couple to a cold plasma device. In an embodiment, a nozzle 1110 is configured to couple to cold plasma device 1210.

In step 1320, a sterile sleeve is attached to a nozzle such that the distal end of the nozzle is enclosed in the sleeve. In an exemplary embodiment, a sterile sleeve 1140 is attached to a nozzle 1110 such that the distal end of the nozzle is enclosed in the sleeve.

In step 1330, the nozzle and sterile sleeve are sterilized. In an embodiment, nozzle 1110 and sterile sleeve 1140 are sterilized.

In step 1340, package nozzle, sterile sleeve and optionally other components, e.g., gas cartridge. In an embodiment, nozzle 1110, sterile sleeve 1140 and optionally other components, e.g., gas cartridge are packaged together.

At step 1340, method 1300 ends.

Figure 14:
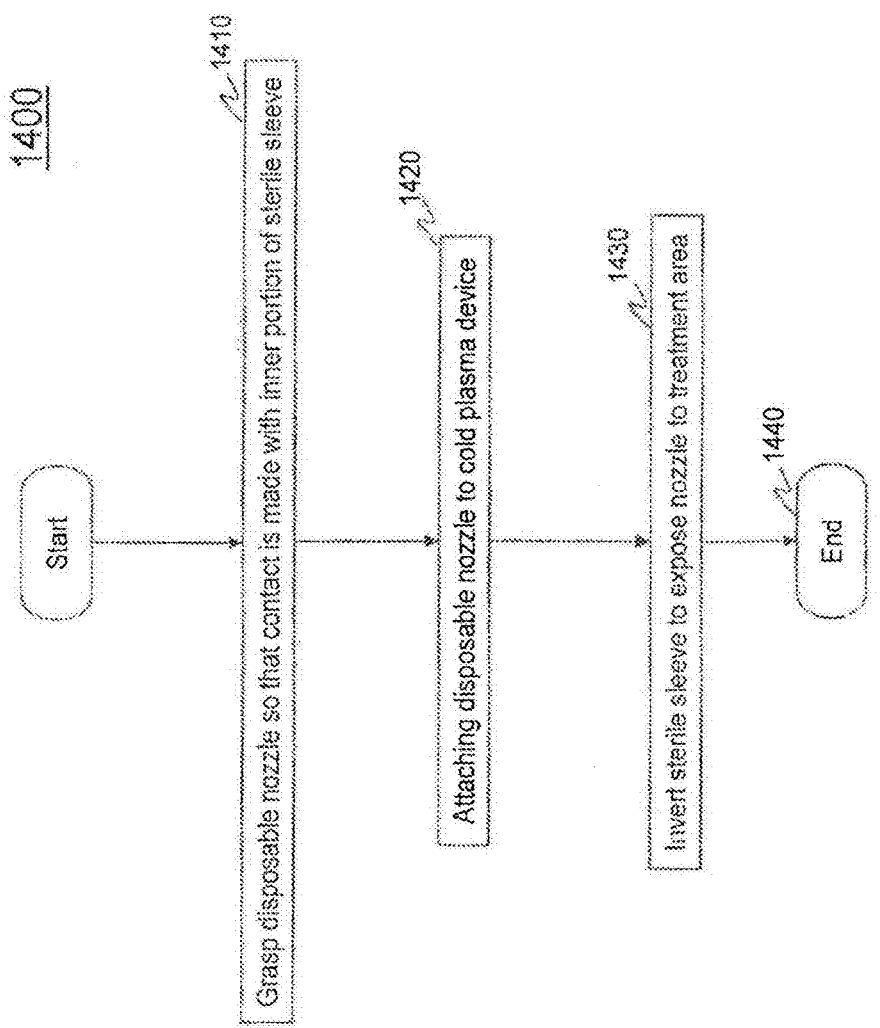
FIG. 14 illustrates a method of use of a nozzle in conjunction with a cold plasma device, in accordance with an embodiment of the present invention.

FIG. 14 provides a flowchart of an exemplary method 1400 to use a disposable nozzle and its sterilized sleeve, according to an embodiment of the present invention.

The process begins at step 1410. In step 1410, the disposable nozzle is grasped via the sterile sleeve so that contact with the disposable nozzle is made through the inner portion of the sterile sleeve. In an embodiment, the disposable nozzle 1110 is grasped via the sterile sleeve 1140 so that contact with the disposable nozzle 1110 is made through the inner portion of the sterile sleeve 1140.

In step 1420, the disposable nozzle is attached to the cold plasma device. In an exemplary embodiment, the disposable nozzle 1110 is attached to the cold plasma device 1210.

In step 1430, the sterile sleeve is inverted to enclose the cold plasma device, a portion of a power cord associated with the cold plasma device, and anything else that requires shielding from the treatment area. In an embodiment, the sterile sleeve 1140 is inverted to enclose the cold plasma device 1210, and a portion of a power cord 1220 associated with the cold plasma device 1210. Thus, disposable nozzle 1110 is not directly touched by the hand of a medical professional. Instead, what begins as the inner portion of the sterile sleeve 1140 becomes the outer portion of the sterile sleeve 1140 when the disposable nozzle is in operation.

At step 1440, method 1400 ends.

Figure 15:
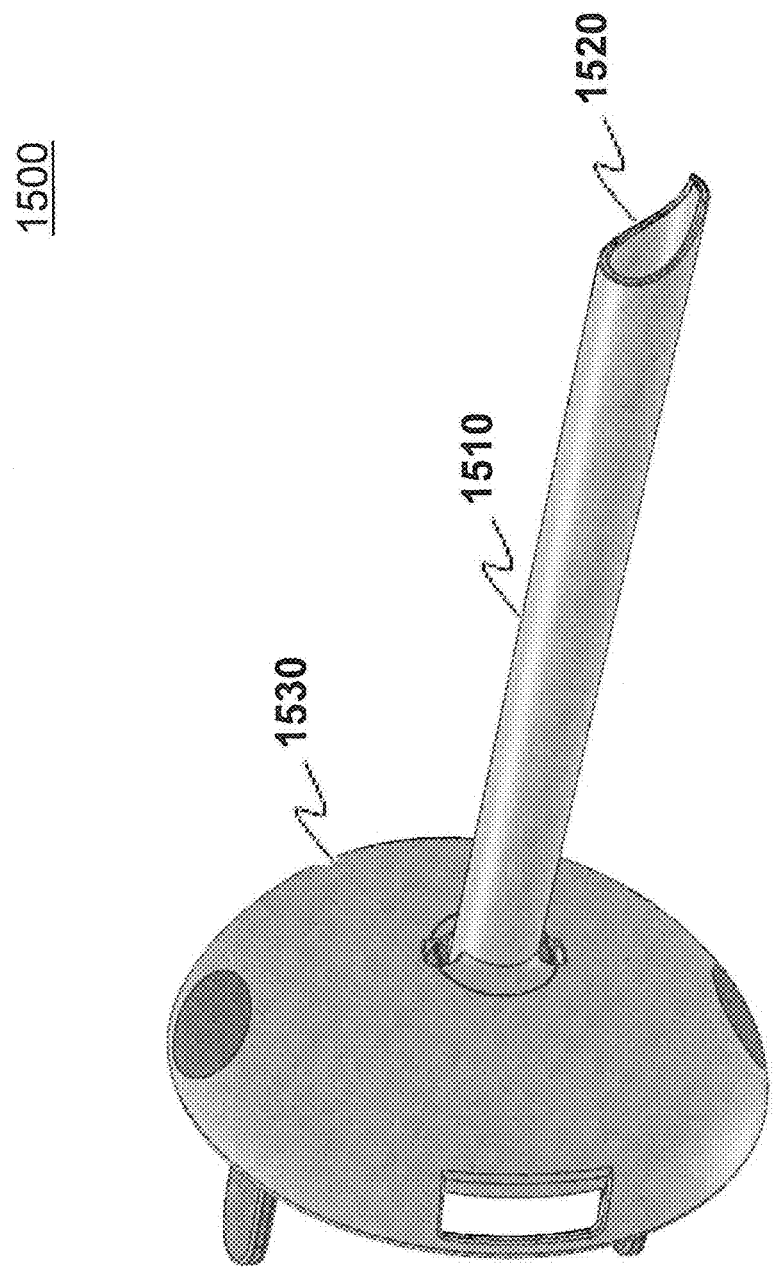
FIG. 15 illustrates an exemplary nozzle that provides shielding, in accordance with an embodiment of the present invention.

Further to the nozzles described above, nozzles with a variety of apertures may be used. FIG. 15 illustrates an exemplary embodiment of a nozzle 1510 with a side-facing aperture 1520. Nozzle 1510 attaches to a cold plasma application device using attachment point 1520. Various embodiments of aperture 1530 fall within the scope of embodiments of the present invention. For example, the various bevel-shaped apertures of hypodermic needles fall within the scope of embodiments of aperture 1520. Thus, aperture 1520 includes the following shapes: A-bevel, B-bevel, C-bevel, bias bevel, chiba bevel, crawford bevel, deflected tip, francine bevel, hustead bevel, huber bevel, trocar bevel and tuchey bevel. Apertures 1520 do not necessarily include the lancet (sharp point of hypodermic) for cold plasma applications described herein.

The various scallop or bevel shapes of aperture 1520 allow for a directional distribution of cold plasma that emanates from nozzle 1510. In such apertures 1520, cold plasma emanates at certain angles while other angles receive little or no cold plasma. Such an asymmetric distribution may be used to, for example, shield a particular biological structure from exposure to cold plasma during a particular treatment. An example of a particular biological structure includes an exposed nerve. In the case of such a biological structure, it is desirable to shield the exposed nerve while still effectively treating the surrounding tissues or biological structures. The extended wall of aperture 1520 would provide the required shielding. In addition, the extended portion of nozzle 1520 (the extended portion being on the opposite side to the bevel aperture) may also be used to manually manipulate tissues or biological structures down in the wound bed prior to or during treatment. In further embodiments, the distal aperture may be positioned with respect to an end of the nozzle such that a proper treatment distance may be maintained from the treatment area.

FIGS. 16(*a*) and 16(*b*) illustrate the shielding effect of nozzle 1510. Referring to FIG. 16(*a*), a photograph of an embodiment of nozzle 1510 is shown. On the aperture side of nozzle 1510 is the treatment zone. On the opposite side of the aperture of nozzle 1510 is the shielded side. FIG. 16(*b*) illustrates the difference in cold plasma treatment when using nozzle 1510. On the aperture side of nozzle 1510, a zone of inhibition is shown. In contrast, on the opposite size of nozzle 1510, the shielded zone is shown.

Many cold plasma treatment processes use a preferred distance between the exit of the cold plasma from a non-bevel aperture to the treatment area so that an optimal plasma formulation is maintained. In such scenarios, the cold plasma application device is configured to not make direct contact with the treatment surface. Nozzle 1510 may also be configured so that the cold plasma emanating from aperture 1520 continues to maintain the optimal plasma treatment distance.

Nozzles 1510 may be manufactured from different materials. Referring to FIG. 17, three different nozzles 1710, 1720, 1730 are shown. Nozzle 1710 may be made from any suitable biocompatible plastic, such as but not limited to acrylonitrile butadiene styrene (ABS), polypropylene (PP), polyethylene (PE), nylon, or similar material, biocompatible non-conductive rapid prototyping material, or material coated with a biocompatible plastic, with the open bevel shaped aperture shown. Indications are that an open bevel shaped aperture is an effective shape for killing bacteria with cold plasma. Suggestions are that this shape, being more open than other shapes, allows for better mixing of the atmosphere with the cold plasma being generated. Nozzle 1720 is made from nylon, and uses a different shaped aperture. Nozzle 1730 may be made from any suitable biocompatible plastic, such as but not limited to acrylonitrile butadiene styrene (ABS), polypropylene (PP), polyethylene (PE), nylon, or similar material, biocompatible non-conductive rapid prototyping material, or material coated with a biocompatible plastic. Each of these materials was used in preliminary testing of nozzles and their respective cold plasma treatment efficiencies. FIG. 18 illustrates two different embodiments of nozzles. Nozzle 1810 is made from nylon and has a shallow bevel-shaped aperture. Nozzle 1820 may be made from any suitable biocompatible plastic, such as but not limited to acrylonitrile butadiene styrene (ABS), polypropylene (PP), polyethylene (PE), nylon, or similar material, biocompatible non-conductive rapid prototyping material, or material coated with a biocompatible plastic and offers a slightly deeper bevel-shaped aperture. Similarly, FIG. 19 illustrates three different embodiments of nozzles. Nozzle 1910 may be made from any suitable biocompatible plastic, such as but not limited to acrylonitrile butadiene styrene (ABS), polypropylene (PP), polyethylene (PE), nylon, or similar material, biocompatible non-conductive rapid prototyping material, or material coated with a biocompatible plastic and has a deep bevel-shaped aperture. Nozzle 1920 is made from nylon and offers a slightly shallower bevel-shaped aperture. Finally, nozzle 1930 is manufactured from nylon and offers a very shallow bevel-shaped aperture. As one of ordinary skill in the art would appreciate, these illustrations are examples, and are not limiting. Various combinations of materials, shapes, and locations fall within the scope of embodiments of the present invention.

FIG. 20 illustrates the directionality and shielding effect of nozzle 1510. Referring to FIG. 20, the cold plasma is visible on the right hand side of the nozzle (the direction of emission of the cold plasma from aperture 1520), while no cold plasma is visible on the left hand side (opposite or shielded side) of nozzle 1510.

FIGS. 21(*a*) and 21(*b*) illustrate the shielding effect of nozzle 1510. Referring to FIG. 21(*a*), the result of the use of a non-beveled aperture is shown. FIG. 21(*b*) shows the results of the use of a beveled aperture, such as that of nozzle 1510.

Initial data has been collected using different nozzle lengths, diameters, nozzle materials, aperture size, cold plasma treatment times, distance of the nozzle from agar during a cold plasma treatment, and location (center versus wall) of nozzle on agar plate during treatment. Performance indicators that were tracked during these early studies included bacterial kill efficiency (in CFU (colony-forming units) per sq. cm.), and area of inhibition zone (sq. cm.). Initial indications show the following. First, a superior bacterial kill result is obtained when the nozzle is immediately adjacent to the agar, versus placed at a distance from the agar. This is not unexpected since plasma effectiveness would decline with increasing distance from the nozzle. Second, a smaller nozzle aperture provides superior bacterial kill results compared with those obtained from a larger nozzle aperture. This may be a result of the higher cold plasma density from the smaller aperture, and the likely increase in cold plasma intensity over the treatment area. Third, a smaller nozzle diameter provides superior bacterial kill results compared with those obtained from a larger nozzle diameter. This may be a result of the higher cold plasma density from the smaller diameter, and the likely increase in cold plasma intensity over the treatment area. In addition, a smaller nozzle diameter provides a larger bacterial inhibition zone area compared with those obtained from a larger nozzle diameter. This may be a result of the increased cold plasma exit speed from the aperture resulting from the smaller diameter, and the likely increase in cold plasma coverage area. Fourth, a longer treatment time provides an increased inhibition zone area compared with a shorter treatment time. This is not unexpected as the longer treatment time provides an opportunity for greater diffusion of the cold plasma to areas further from the aperture of the nozzle. Finally, early results indicate that nozzle material may play a role in the efficacy of cold plasma treatment using nozzle apertures. A nozzle made from nylon has shown superior bacterial kill efficiency for the same size inhibition zone, when compared to a similar nozzle made from a polymer material. It is assumed that the polymer material may interact with the cold plasma (e.g., oxidation, etching by the cold plasma) to the detriment of the effectiveness of the cold plasma. As noted above, indications are that an open bevel shaped aperture is an effective shape for killing bacteria with cold plasma. Suggestions are that this shape, being more open than other shapes, allows for better mixing of the atmosphere with the cold plasma being generated. Further investigations are planned to shed additional light on improvement of the performance of cold plasma treatments using nozzles.

As one of ordinary skill in the art would recognize, the innovative apertures described above may be used separately, or in conjunction with other innovative approaches described above in this specification. For example, these apertures may be used with disks, with foam-like materials, with cannula tubes, and with sleeves and shrouds. Furthermore, more than one of these apertures may be used together in one nozzle for certain cold plasma treatment processes. Two or more of these apertures may direct cold plasma in the same direction, in differing directions, or in opposite directions, as required by the cold plasma treatment process(es) and treatment area(s).

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A cold plasma application device, comprising:
   a cold plasma generation device having a cold plasma outlet port; and
   a nozzle having a proximal aperture, a distal aperture and a solid wall located at the distal aperture, the proximal aperture configured to be coupled to the cold plasma outlet port to receive cold plasma from the cold plasma generation device, the distal aperture being non-perpendicular to a longitudinal axis of the nozzle, wherein cold plasma is directed by the distal aperture to a treatment area, and wherein the solid wall precludes cold plasma from contacting a non-treatment area.

2. The cold plasma application device of claim 1, wherein the distal aperture comprises an open bevel shape.

3. The cold plasma application device of claim 2, wherein the open bevel shape comprises one of A-bevel, B-bevel, C-bevel, bias bevel, chiba bevel, crawford bevel, francine bevel, hustead bevel, huber bevel, trocar bevel and tuchey bevel shapes.

4. The cold plasma application device of claim 1, wherein the distal aperture is located with respect to an end of the nozzle such that a predetermined treatment distance between the end of the nozzle and the treatment area is indicated.

5. The cold plasma application device of claim 1, wherein the nozzle comprises at least one of acrylonitrile butadiene styrene (ABS), polypropylene (PP), polyethylene (PE), nylon, or other biocompatible material.

6. The cold plasma application device of claim 1, wherein the nozzle further comprises:
   a disk positioned in the nozzle between the proximal aperture and the distal aperture, the disk comprising a material having a plurality of sub-apertures embedded therein such that a stable cold plasma plume exits from the distal aperture.

7. The cold plasma application device of claim 6, wherein the material comprises a foam-like material.

8. The cold plasma application device of claim 6, wherein the material further comprises at least one of water, saline solution, hydrogen peroxide, antibiotic solutions, anesthetics, and haemostatic agents.

9. The cold plasma application device of claim 1, wherein the nozzle comprises a cannula tube.

10. The cold plasma application device of claim 1, wherein the nozzle is detachable.

11. A method, comprising:
    coupling a nozzle to a cold plasma generation device, the nozzle having a proximal aperture, a distal aperture and a solid wall located at the distal aperture, the proximal aperture configured to be coupled to an outlet port of the cold plasma generation device to receive cold plasma from the cold plasma generation device, the distal aperture being non-perpendicular to a longitudinal axis of the nozzle, wherein cold plasma is directed by the distal aperture to a treatment area, and wherein the solid wall precludes cold plasma from contacting a non-treatment area.

12. The method of claim 11, further comprising:
    using the nozzle to manually manipulate tissues in the treatment area.

13. The method of claim 11, wherein the distal aperture comprises an open bevel shape.

14. The method of claim 13, wherein the open bevel shape comprises one of A-bevel, B-bevel, C-bevel, bias bevel, chiba bevel, crawford bevel, francine bevel, hustead bevel, huber bevel, trocar bevel and tuchey bevel shapes.

15. The method of claim 11, wherein the distal aperture is located with respect to an end of the nozzle such that a predetermined treatment distance between the end of the nozzle and the treatment area is indicated.

16. The method of claim 11, wherein the nozzle comprises at least one of acrylonitrile butadiene styrene (ABS), polypropylene (PP), polyethylene (PE), nylon, or other biocompatible material.

17. The method of claim 11, wherein the nozzle further comprises:
  a disk positioned in the nozzle between the proximal aperture and the distal aperture, the disk comprising a material having a plurality of sub-apertures embedded therein such that a stable cold plasma plume exits from the distal aperture.

18. The method of claim 17, wherein the material comprises a foam-like material.

19. The method of claim 17, wherein the material further comprises at least one of water, saline solution, hydrogen peroxide, antibiotic solutions, anesthetics, and haemostatic agents.

20. The method of claim 11, wherein the nozzle comprises a cannula tube.

* * * * *